US012629219B2

(12) United States Patent
Takazawa et al.

(10) Patent No.: US 12,629,219 B2
(45) Date of Patent: May 19, 2026

(54) PROCESSING SYSTEM, ENDOSCOPE SYSTEM, AND PROCESSING METHOD

(71) Applicant: OLYMPUS CORPORATION, Tokyo (JP)

(72) Inventors: Naohiro Takazawa, Kokubunji (JP); Hidetoshi Nishimura, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 151 days.

(21) Appl. No.: 18/432,529

(22) Filed: Feb. 5, 2024

(65) Prior Publication Data

US 2025/0064533 A1 Feb. 27, 2025

Related U.S. Application Data

(60) Provisional application No. 63/534,537, filed on Aug. 24, 2023.

(51) Int. Cl.
*A61B 34/00* (2016.01)
*A61B 1/00* (2006.01)
(Continued)

(52) U.S. Cl.
CPC ........ *A61B 34/25* (2016.02); *A61B 1/000094* (2022.02); *A61B 1/000096* (2022.02);
(Continued)

(58) Field of Classification Search
CPC ........ A61B 1/000094; A61B 1/000096; A61B 1/0005; A61B 1/273; A61B 34/25; A61B 2034/107; A61B 2034/252; G06T 7/50; G06T 11/00; G06T 2207/10028; G06T 2207/10068; G06T 2207/20081;
(Continued)

(56) References Cited

U.S. PATENT DOCUMENTS

2016/0331454 A1* 11/2016 Kobayashi ......... A61B 18/1492
2017/0143734 A1* 5/2017 De Colle ............. A61K 31/198
2023/0090573 A1* 3/2023 Legum ............... A61B 18/1487
604/96.01
(Continued)

FOREIGN PATENT DOCUMENTS

JP 2001-167272 A 6/2001
JP 2021048927 A * 4/2021 ............... G06T 7/00

OTHER PUBLICATIONS

Chen et al. "Duodenal major papilla morphology can affect biliary cannulation and complications during ERCP, an observational study", Sep. 23, 2020, BMC Gastroenterology, doi: 10.1186/s12876-020-01455-0 (Year: 2020).*
(Continued)

*Primary Examiner* — Kee M Tung
*Assistant Examiner* — Thang Gia Huynh
(74) *Attorney, Agent, or Firm* — Scully, Scott, Murphy & Presser, P.C.

(57) ABSTRACT

A processing system includes a processor including hardware. The processor acquires an endoscope image in which a duodenal papilla including an oral protrusion is imaged, estimates a depth map of a region including the duodenal papilla from the endoscope image, estimates a summit line of the oral protrusion from the estimated depth map, and performs display processing so as to superimpose a guide display based on the estimated summit line on the endoscope image.

20 Claims, 42 Drawing Sheets

(51) Int. Cl.

| | |
|---|---|
| *A61B 1/273* | (2006.01) |
| *A61B 34/10* | (2016.01) |
| *G06T 7/50* | (2017.01) |
| *G06T 11/00* | (2026.01) |

(52) U.S. Cl.

CPC .............. *A61B 1/0005* (2013.01); *G06T 7/50* (2017.01); *G06T 11/00* (2013.01); *A61B 1/273* (2013.01); *A61B 2034/107* (2016.02); *A61B 2034/252* (2016.02); *G06T 2207/10028* (2013.01); *G06T 2207/10068* (2013.01); *G06T 2207/20081* (2013.01); *G06T 2207/30028* (2013.01); *G06T 2210/41* (2013.01)

(58) Field of Classification Search

CPC ........... G06T 2207/30028; G06T 2207/30092; G06T 2207/20084; G06T 2210/41

See application file for complete search history.

(56) References Cited

U.S. PATENT DOCUMENTS

2023/0346199 A1* 11/2023 Kristensen ............. A61B 34/25

OTHER PUBLICATIONS

Ozyoruk et al. "EndoSLAM Dataset and An Unsupervised Monocular Visual Odometry and Depth Estimation Approach for Endoscopic Videos: Endo-SfM Learner", Oct. 1, 2020, https://doi.org/10.48550/arXiv.2006.16670 (Year: 2020).*

* cited by examiner

ESOPHAGUS

LIVER

GALLBLADDER

INSERTION PORTION OF
ENDOSCOPE

BILE DUCT

DUODENUM

ENDOSCOPE TIP

PANCREAS

PAPILLARY PORTION

PANCREATIC DUCT

FIG.3
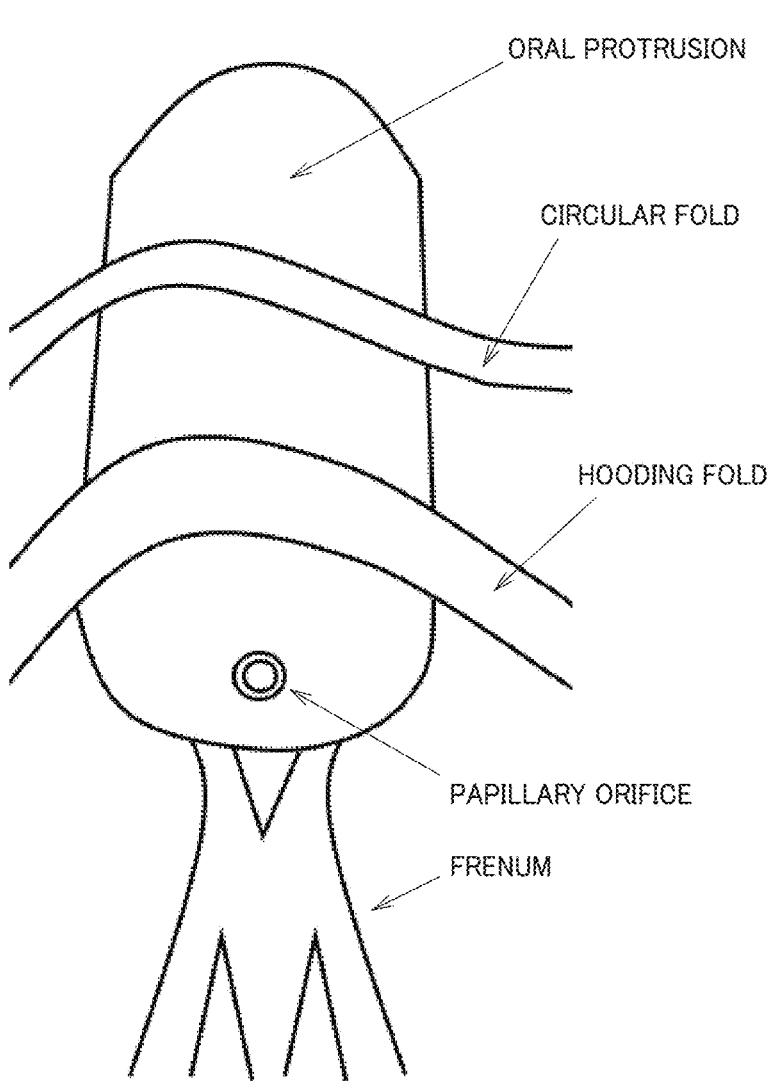
ORAL PROTRUSION
CIRCULAR FOLD
HOODING FOLD
PAPILLARY ORIFICE
FRENUM
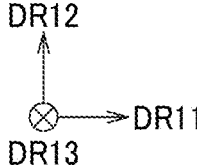
DR12
DR13 ⊗ → DR11

FIG.4
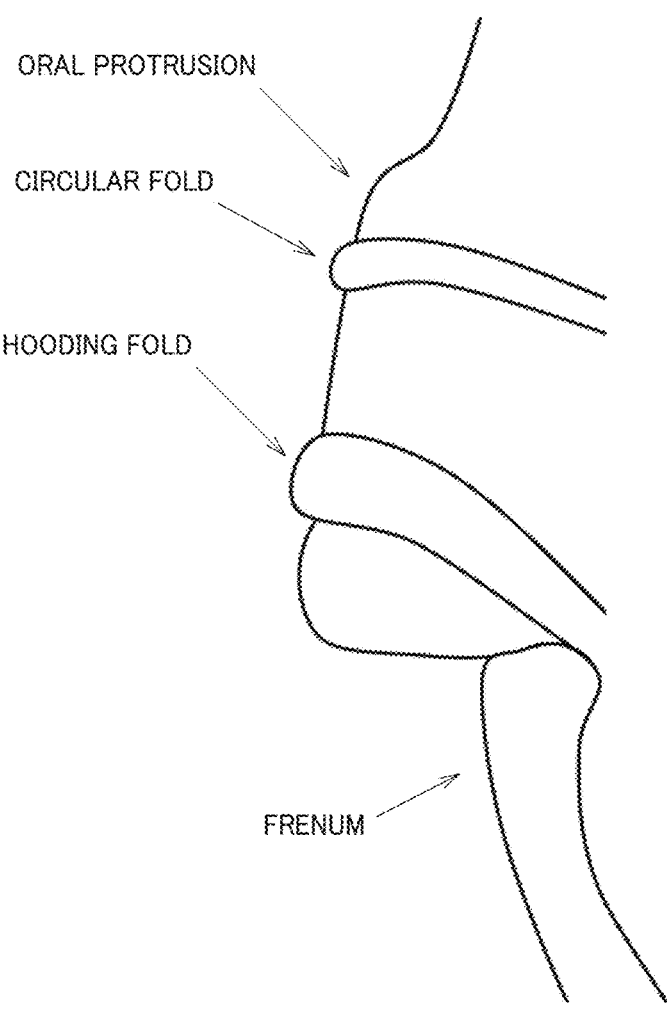
ORAL PROTRUSION
CIRCULAR FOLD
HOODING FOLD
FRENUM
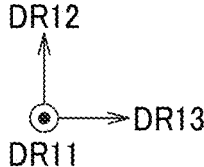

FIG.5
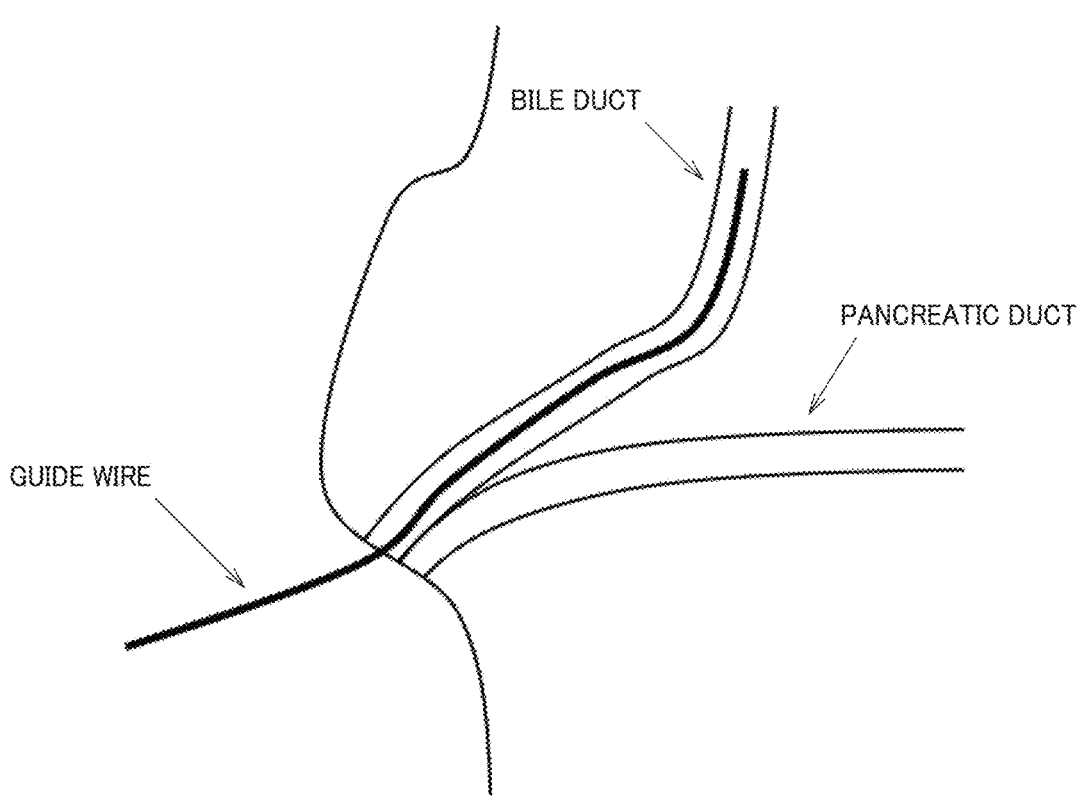
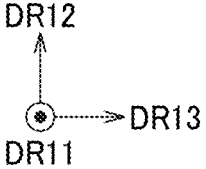

FIG.9

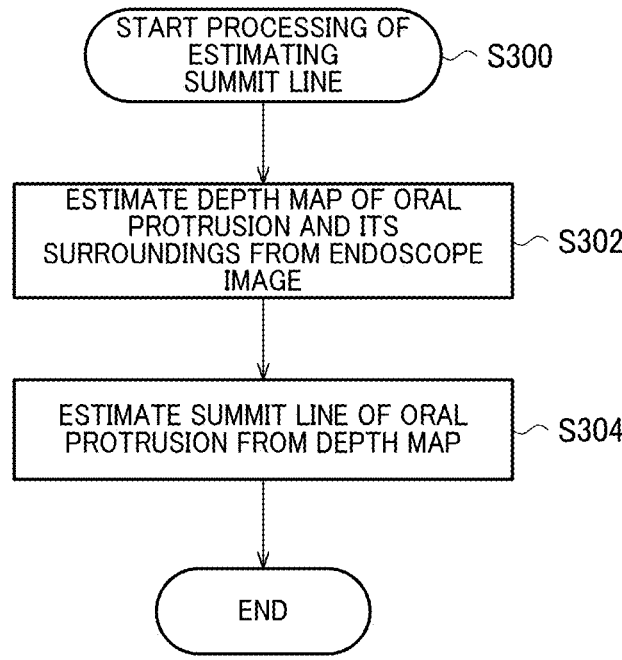

```
   ┌─────────────────────┐
   │  START PROCESSING OF │
   │      ESTIMATING      │─── S300
   │     SUMMIT LINE      │
   └─────────────────────┘
              │
              ▼
   ┌─────────────────────┐
   │ ESTIMATE DEPTH MAP OF ORAL │
   │   PROTRUSION AND ITS       │─── S302
   │ SURROUNDINGS FROM ENDOSCOPE│
   │         IMAGE              │
   └─────────────────────┘
              │
              ▼
   ┌─────────────────────┐
   │ ESTIMATE SUMMIT LINE OF ORAL │─── S304
   │ PROTRUSION FROM DEPTH MAP    │
   └─────────────────────┘
              │
              ▼
   ┌─────────────────────┐
   │         END         │
   └─────────────────────┘
```

FIG.10

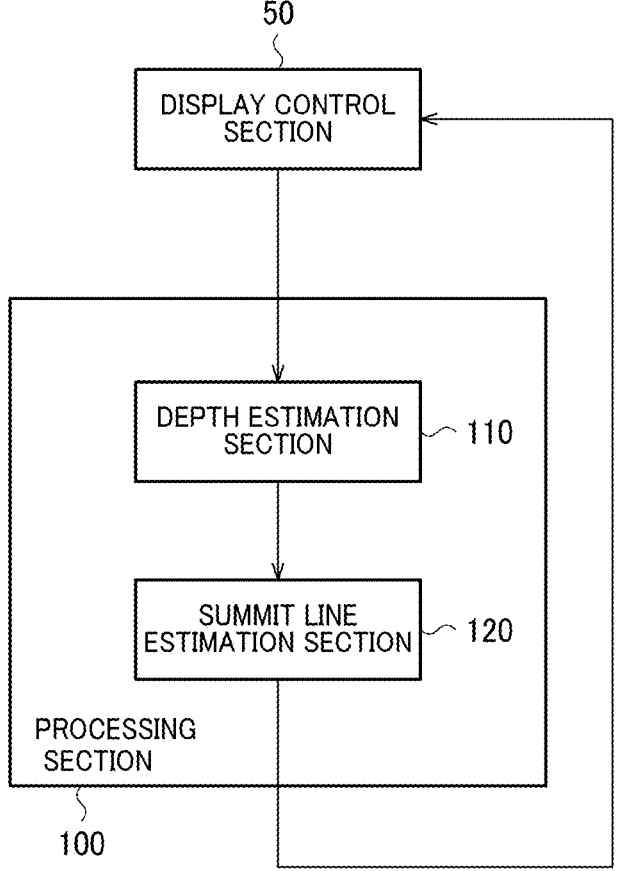

```
                    50
   ┌──────────────────┐
   │ DISPLAY CONTROL  │◄──────────┐
   │     SECTION      │           │
   └──────────────────┘           │
              │                   │
              ▼                   │
   ┌────────────────────────┐     │
   │                        │     │
   │  ┌──────────────────┐  │     │
   │  │ DEPTH ESTIMATION │──┼─ 110 │
   │  │     SECTION      │  │     │
   │  └──────────────────┘  │     │
   │           │            │     │
   │           ▼            │     │
   │  ┌──────────────────┐  │     │
   │  │  SUMMIT LINE     │──┼─ 120 │
   │  │ ESTIMATION SECTION│ │     │
   │  └──────────────────┘  │     │
   │                        │     │
   │ PROCESSING             │     │
   │ SECTION                │─────┘
   └────────────────────────┘
              │
            100
```

FIG.13
A31
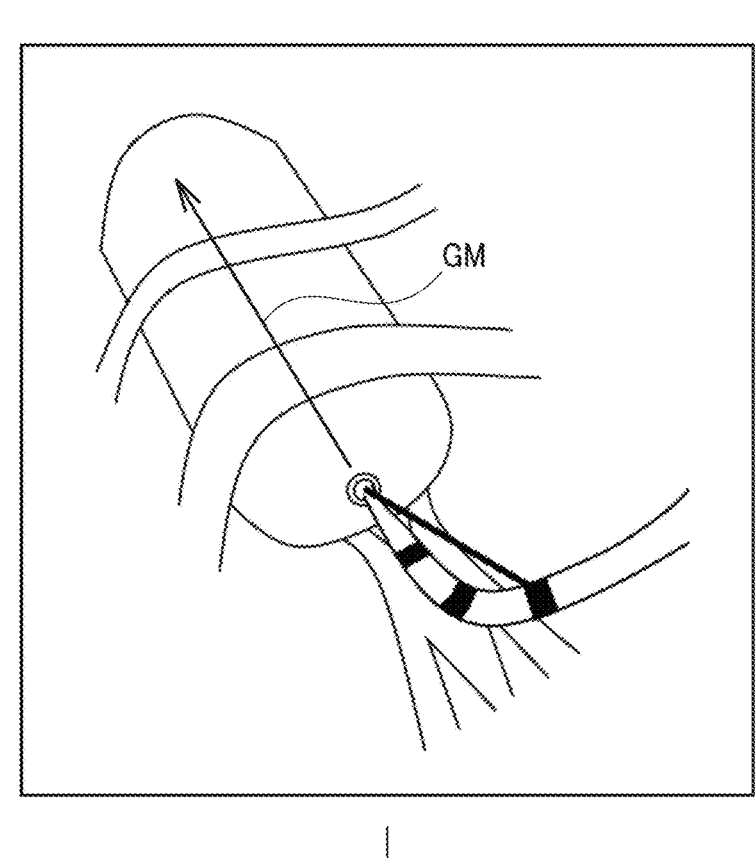
GM
A32
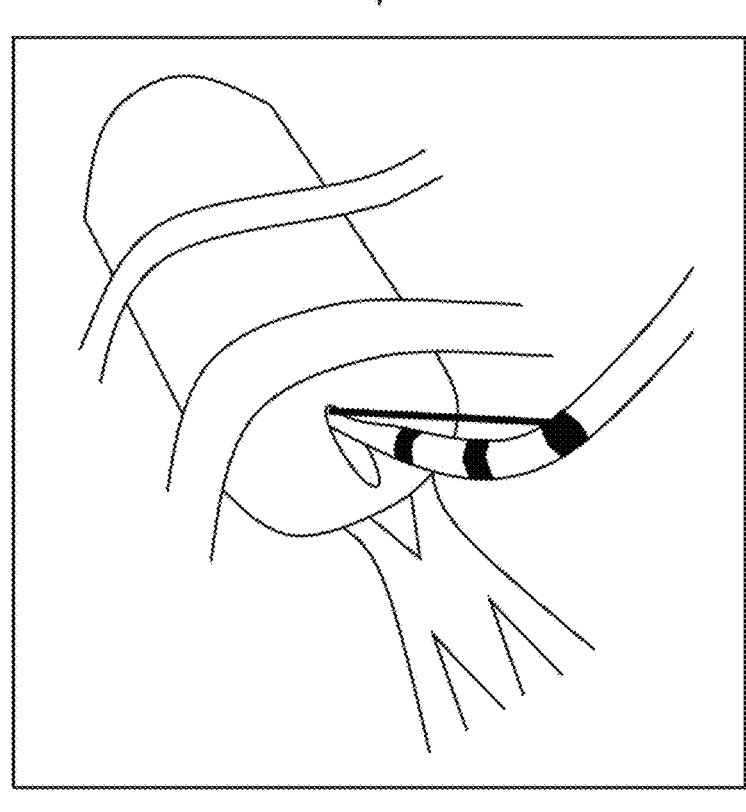

DUODENUM

PAPILLARY PORTION

ENDOSCOPE TIP

C2

C1

JEJUNUM

DEGREE OF ACCURACY OF
SEGMENTATION:○○%

1

PROCESSING SYSTEM, ENDOSCOPE SYSTEM, AND PROCESSING METHOD

CROSS REFERENCE TO RELATED APPLICATIONS

This application is based upon and claims the benefit of priority to U.S. Provisional Patent Application No. 63/534, 537 filed on Aug. 24, 2023, the entire contents of which are incorporated herein by reference.

BACKGROUND OF THE INVENTION

Known is a method of performing a treatment on bile duct cancer or the like using an endoscope. Japanese Unexamined Patent Application Publication No. 2001-167272 discloses a method of using a three dimensional endoscope to estimate a three dimensional shape of the duodenal papilla.

SUMMARY OF THE INVENTION

In accordance with one of some aspect, there is provided a processing system comprising:
  a processor including hardware,
  the processor being configured to
  acquire an endoscope image in which a duodenal papilla including an oral protrusion is imaged;
  estimate a depth map of a region including the duodenal papilla from the endoscope image;
  estimate a summit line of the oral protrusion from the estimated depth map; and
  perform display processing so as to superimpose a guide display based on the estimated summit line on the endoscope image.
In accordance with one of some aspect, there is provided an endoscope system comprising:
  the processing system as defined above; and
  an endoscope.
In accordance with one of some aspect, there is provided a processing method comprising:
  performing processing of acquiring an endoscope image in which a duodenal papilla including an oral protrusion is imaged;
  performing processing of estimating a depth map of a region including the duodenal papilla from the endoscope image;
  performing processing of estimating a summit line of the oral protrusion from the estimated depth map; and
  performing display processing so as to superimpose a guide display based on the estimated summit line on the endoscope image.

BRIEF DESCRIPTION OF THE DRAWINGS

FIG. 1 is a diagram for describing a configuration example of a processing system or the like.
FIG. 3 is a view for schematically describing the duodenal papilla.
FIG. 4 is another view for schematically describing the duodenal papilla.
FIG. 5 is a view for schematically describing the duodenal papilla and the like when the EST is performed.

2

Figure 7:
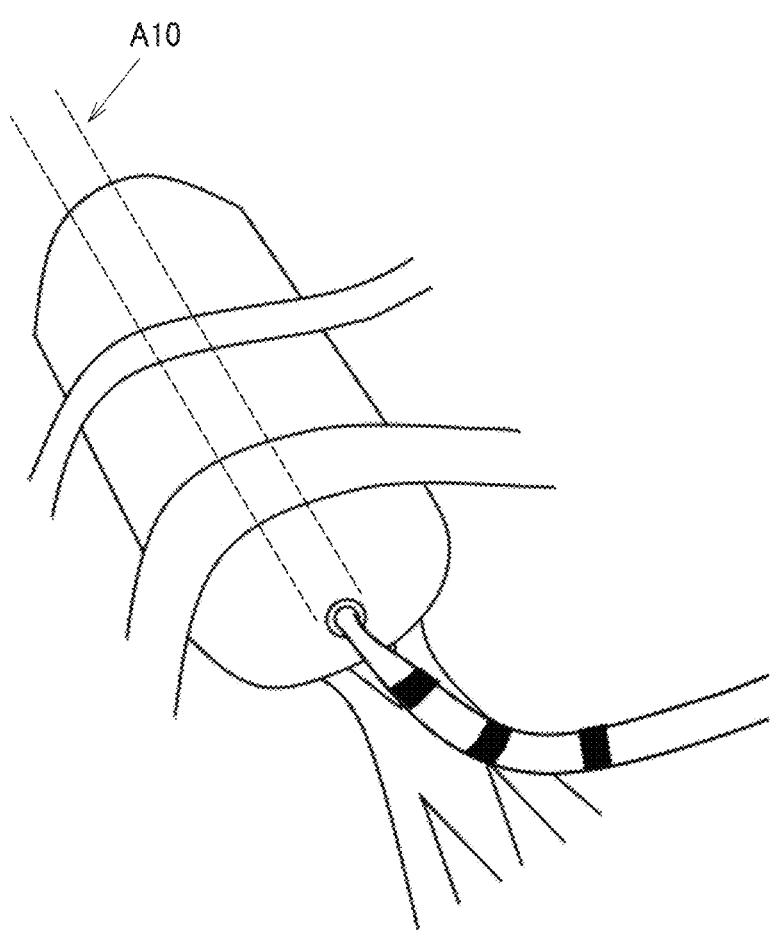
Figure 8:
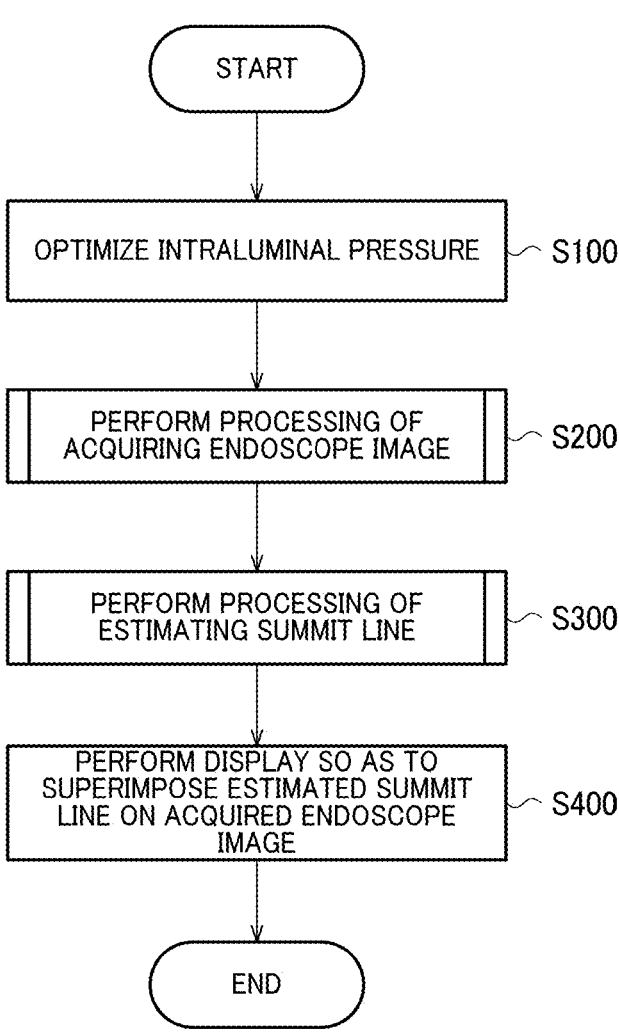
Figure 11:
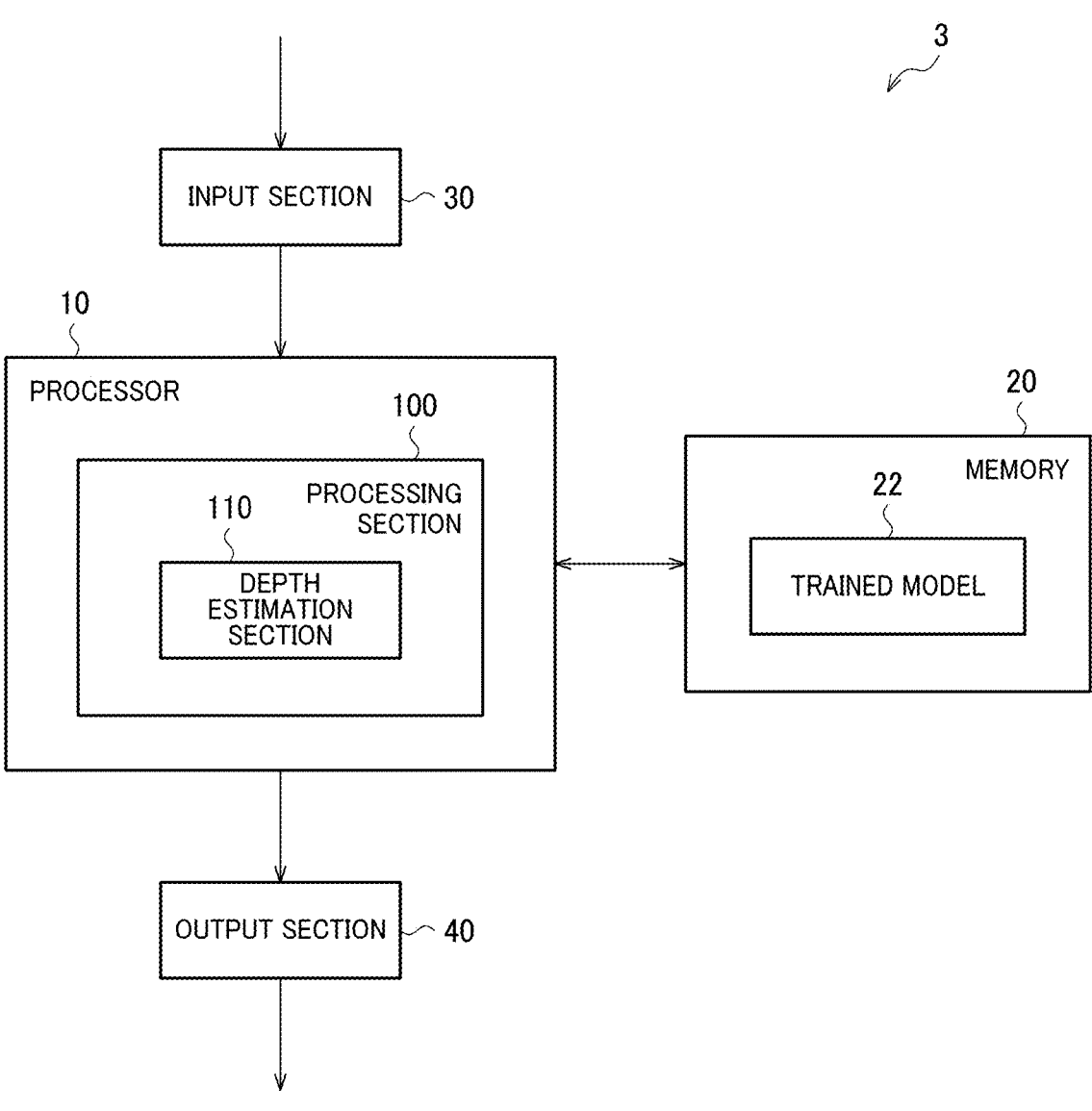
Figure 12:
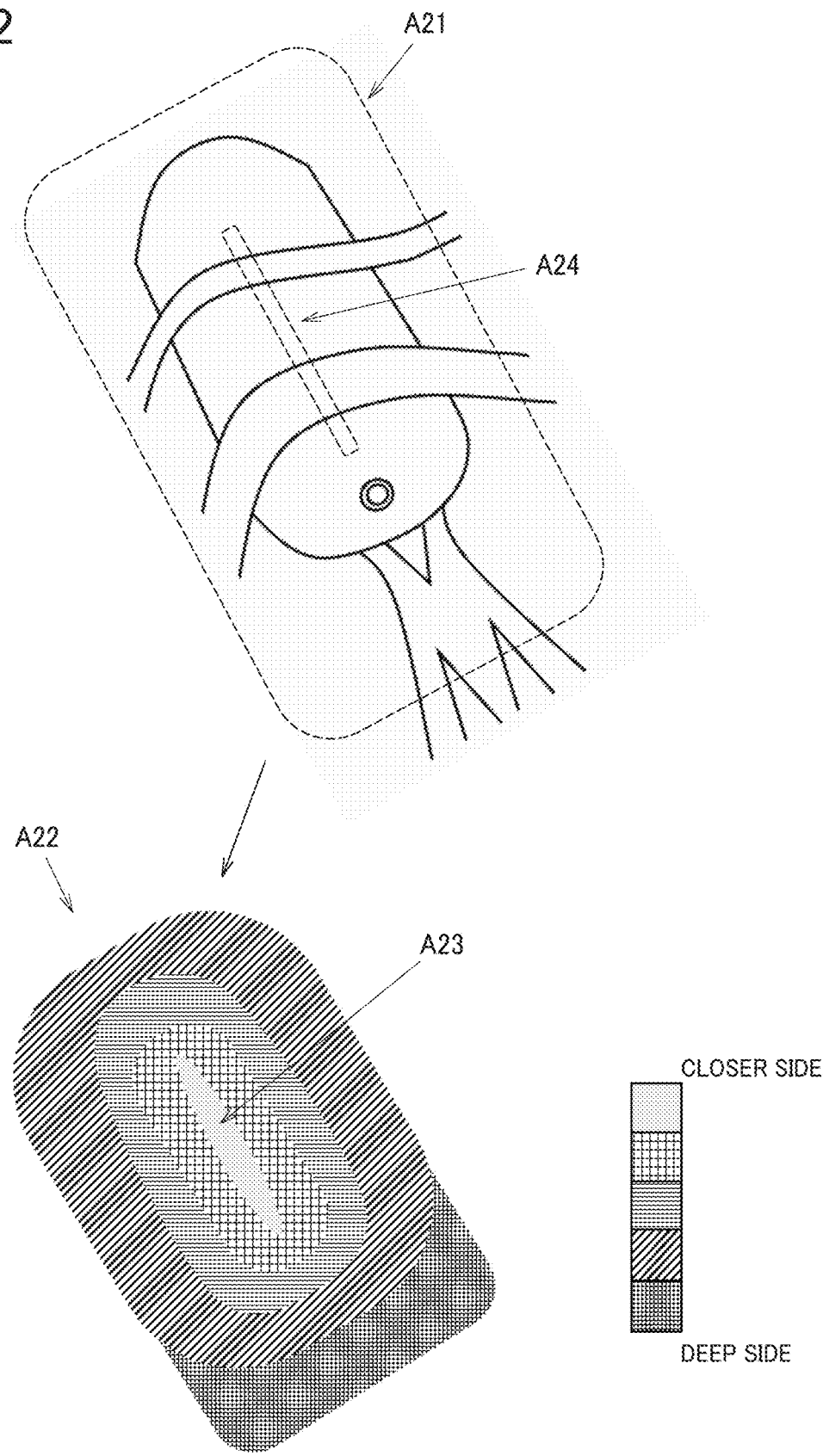
Figure 14:
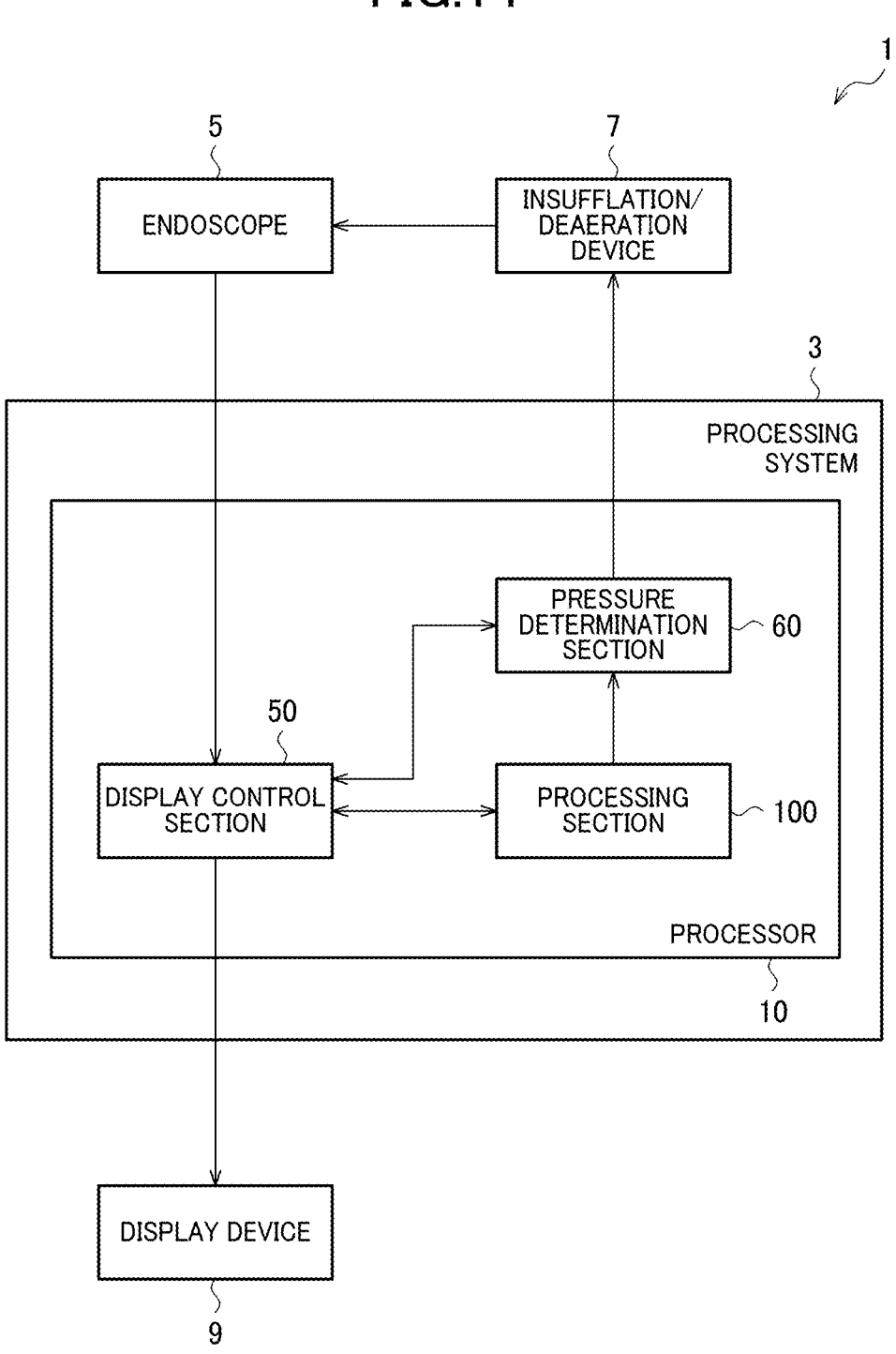
Figure 15:
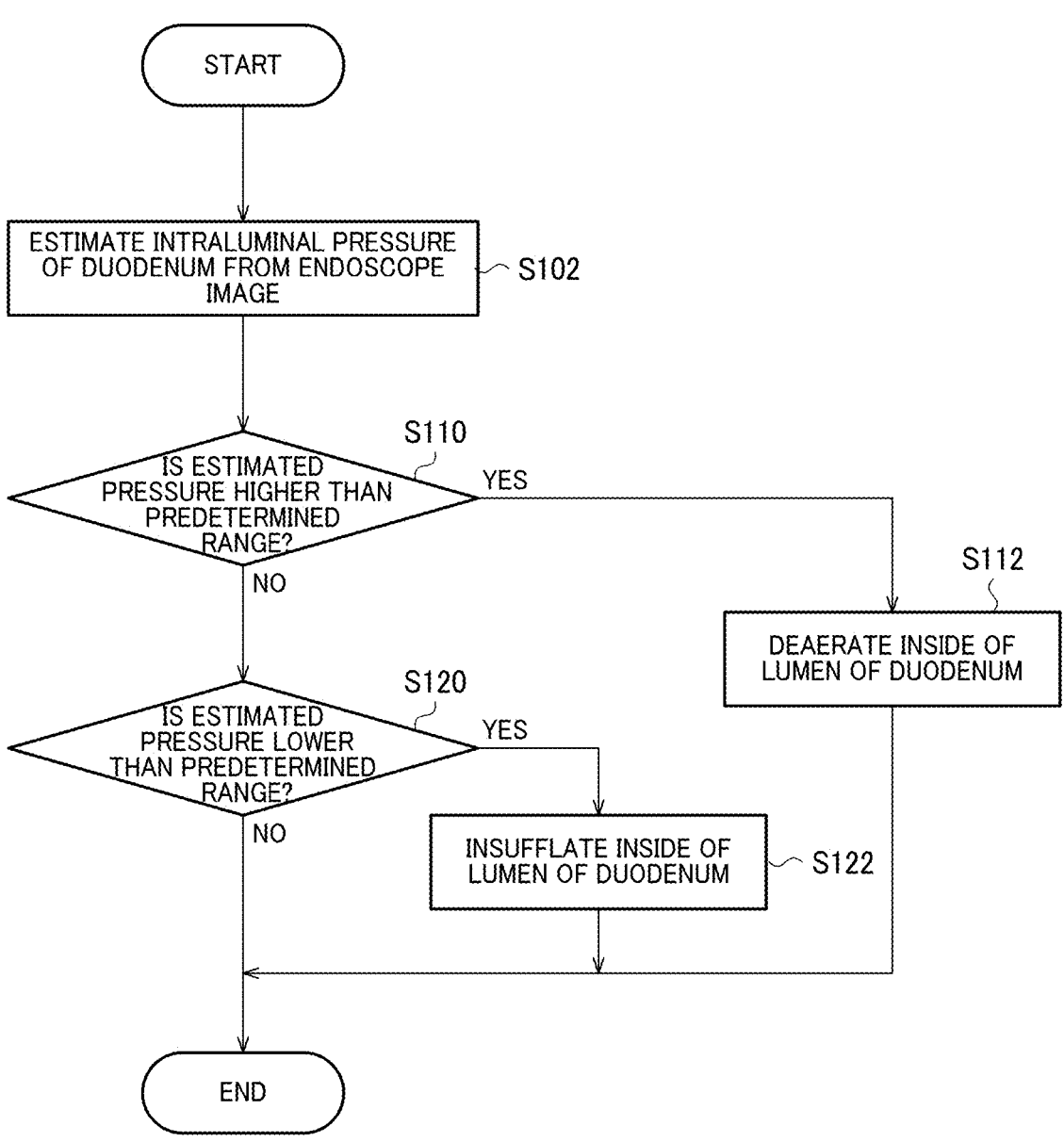
Figure 16:
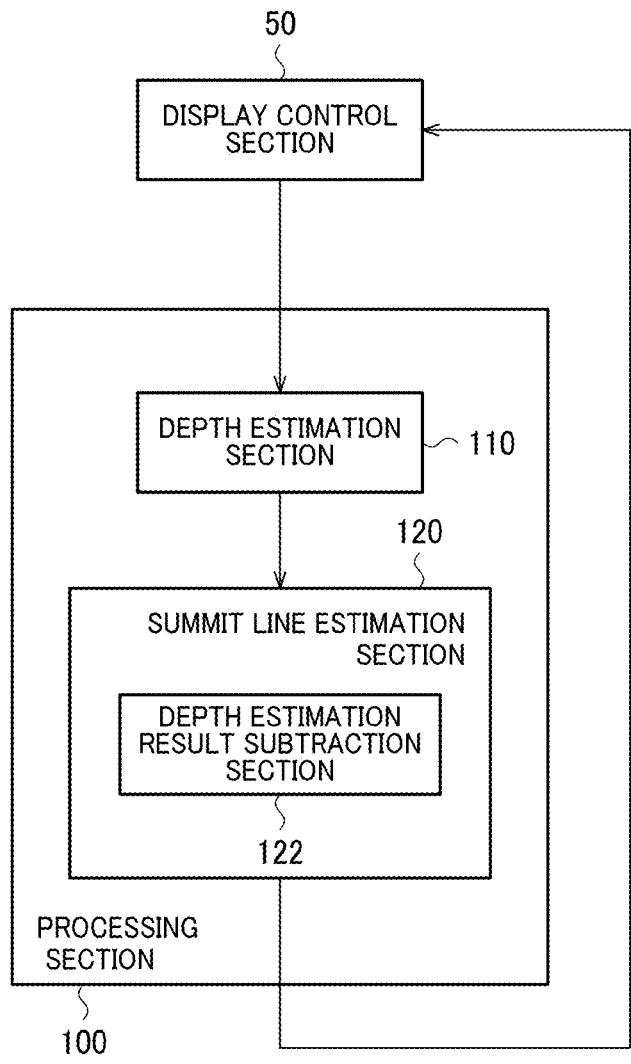
Figure 17:
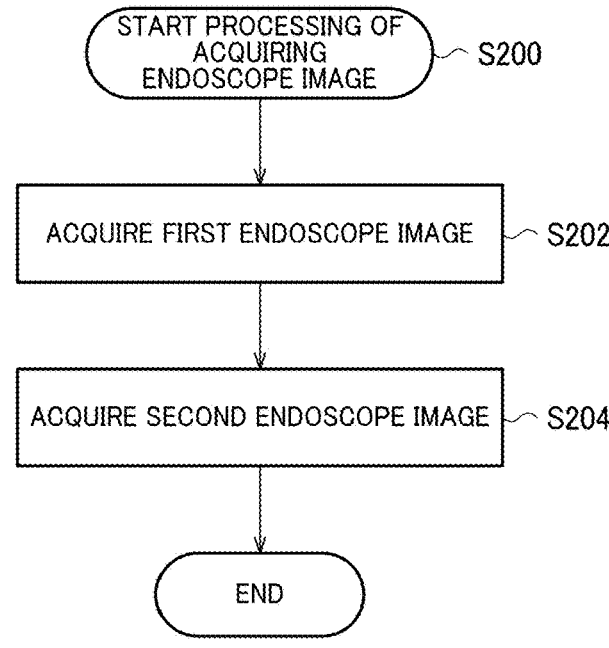
Figure 18:
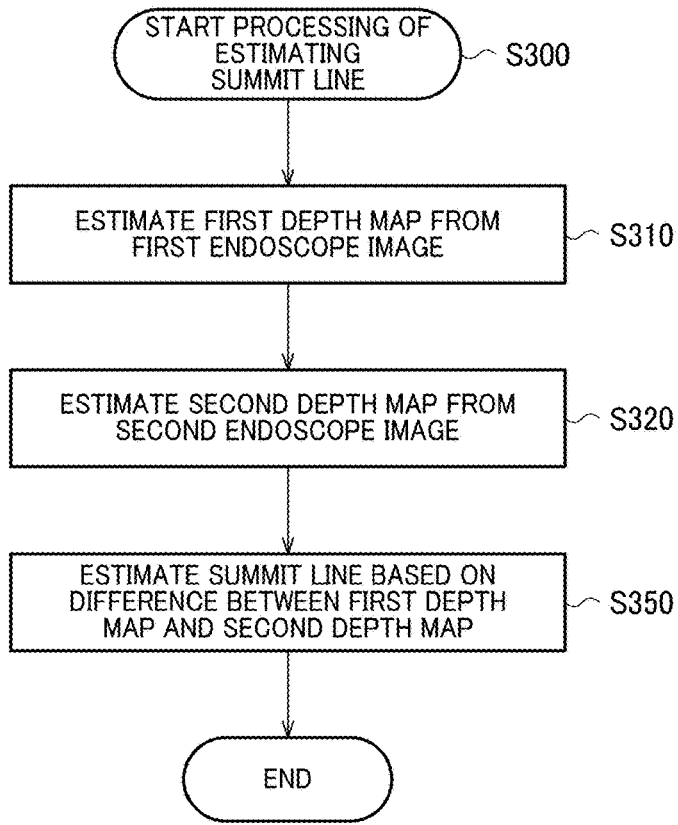
Figure 19:
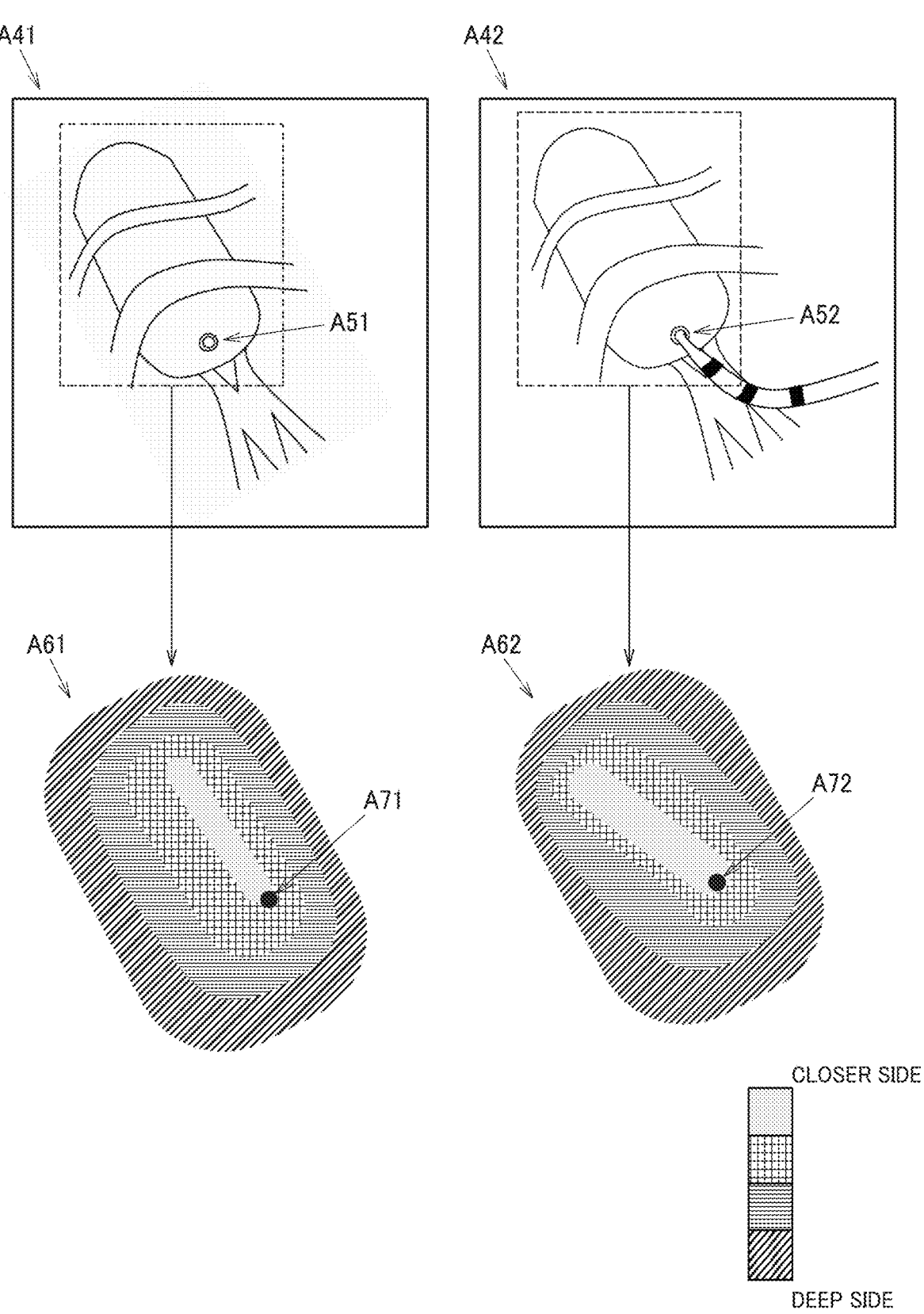
Figure 20:
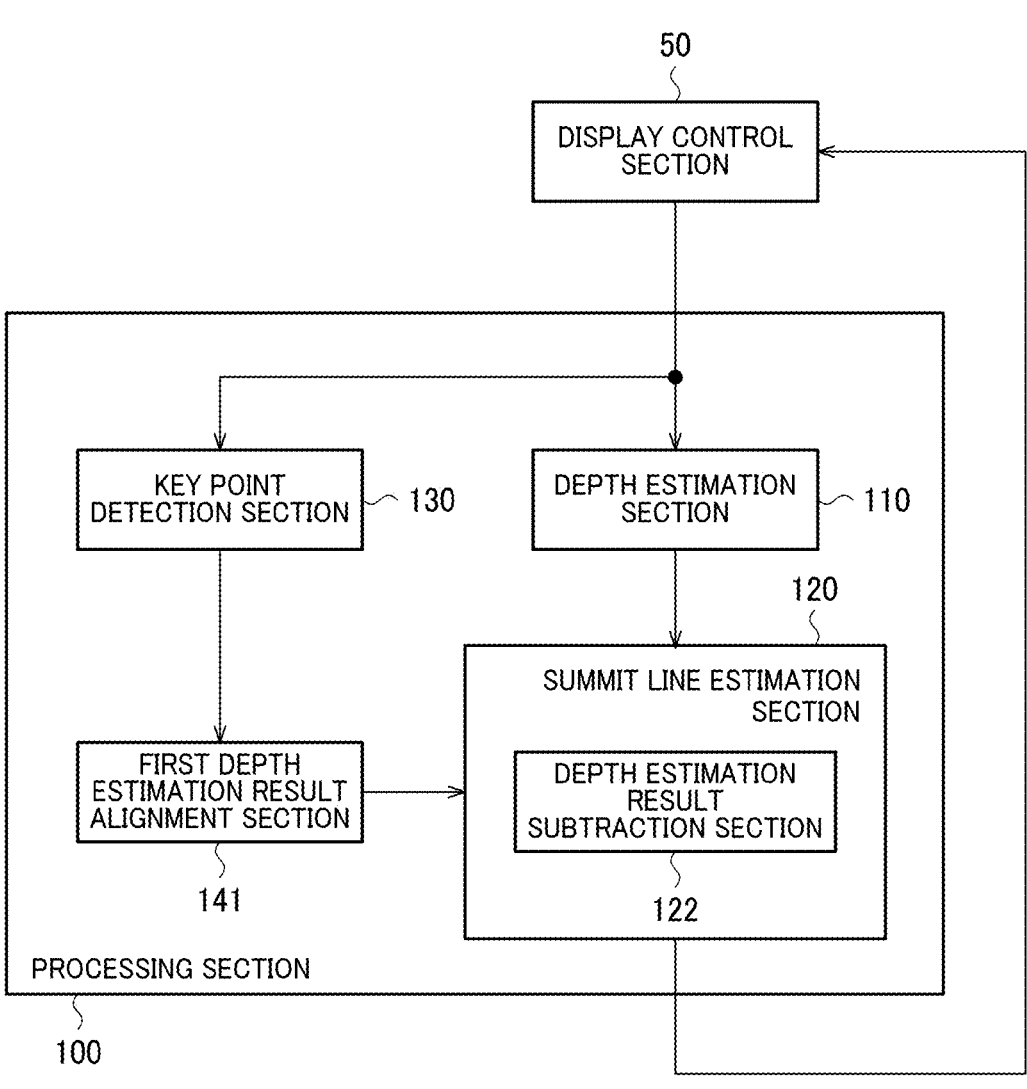
Figure 21:
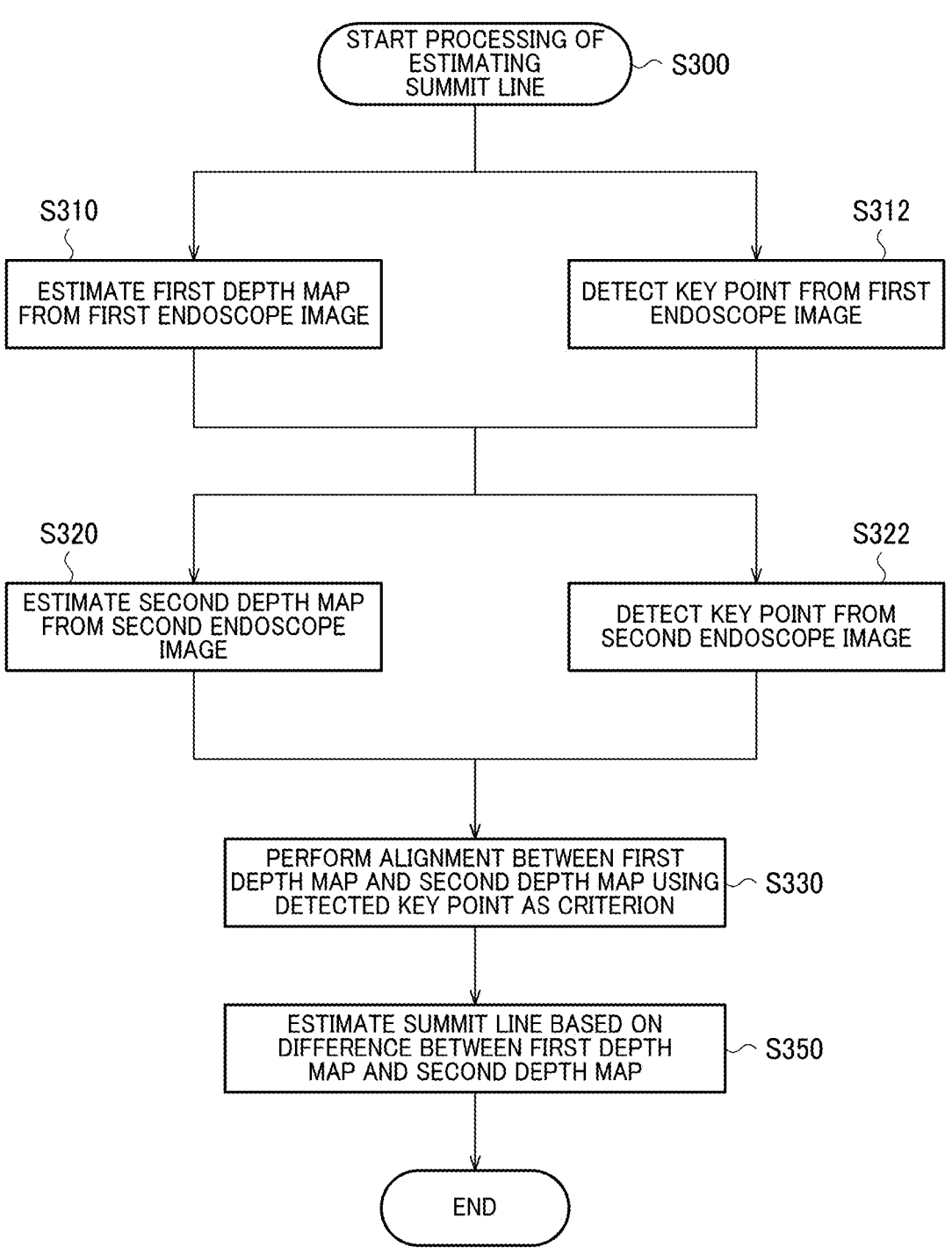
Figure 22:
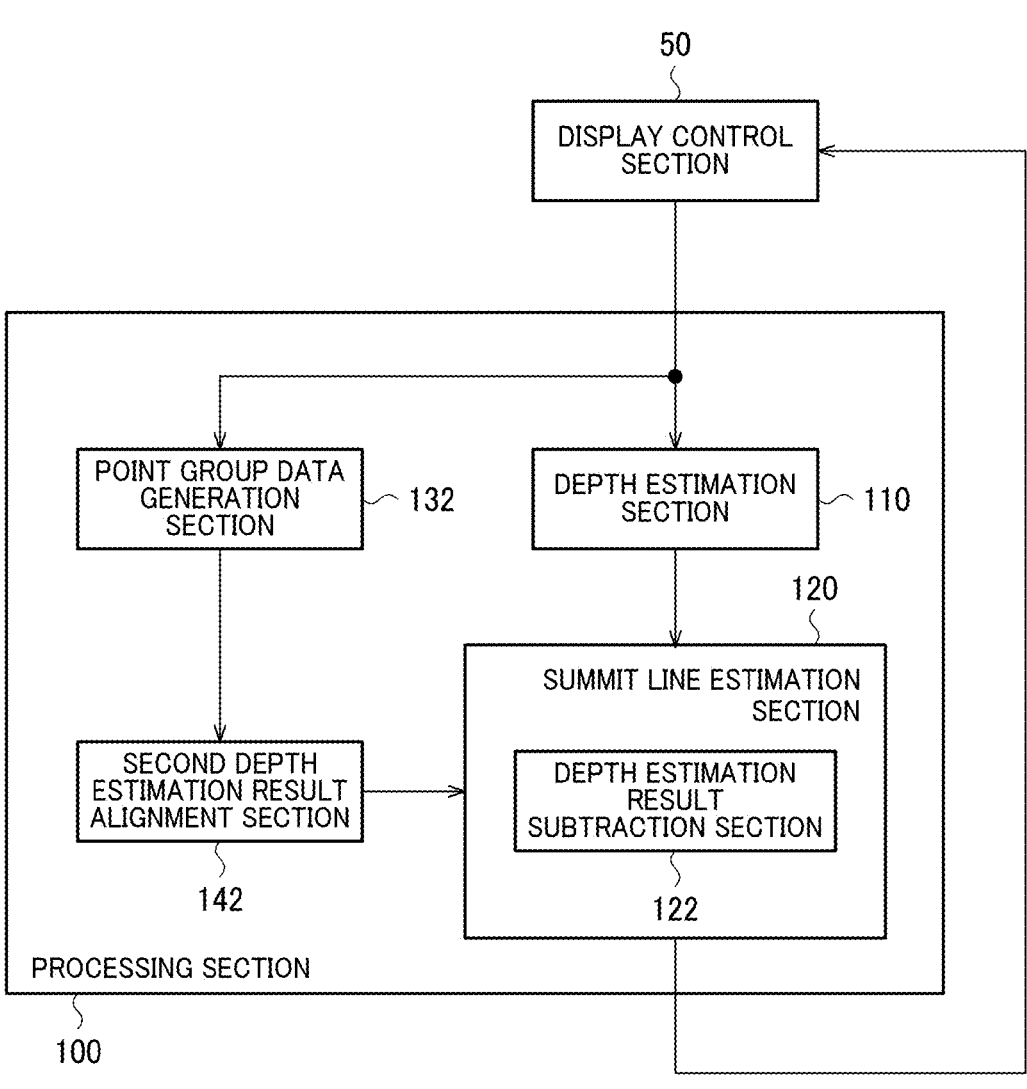
Figure 23:
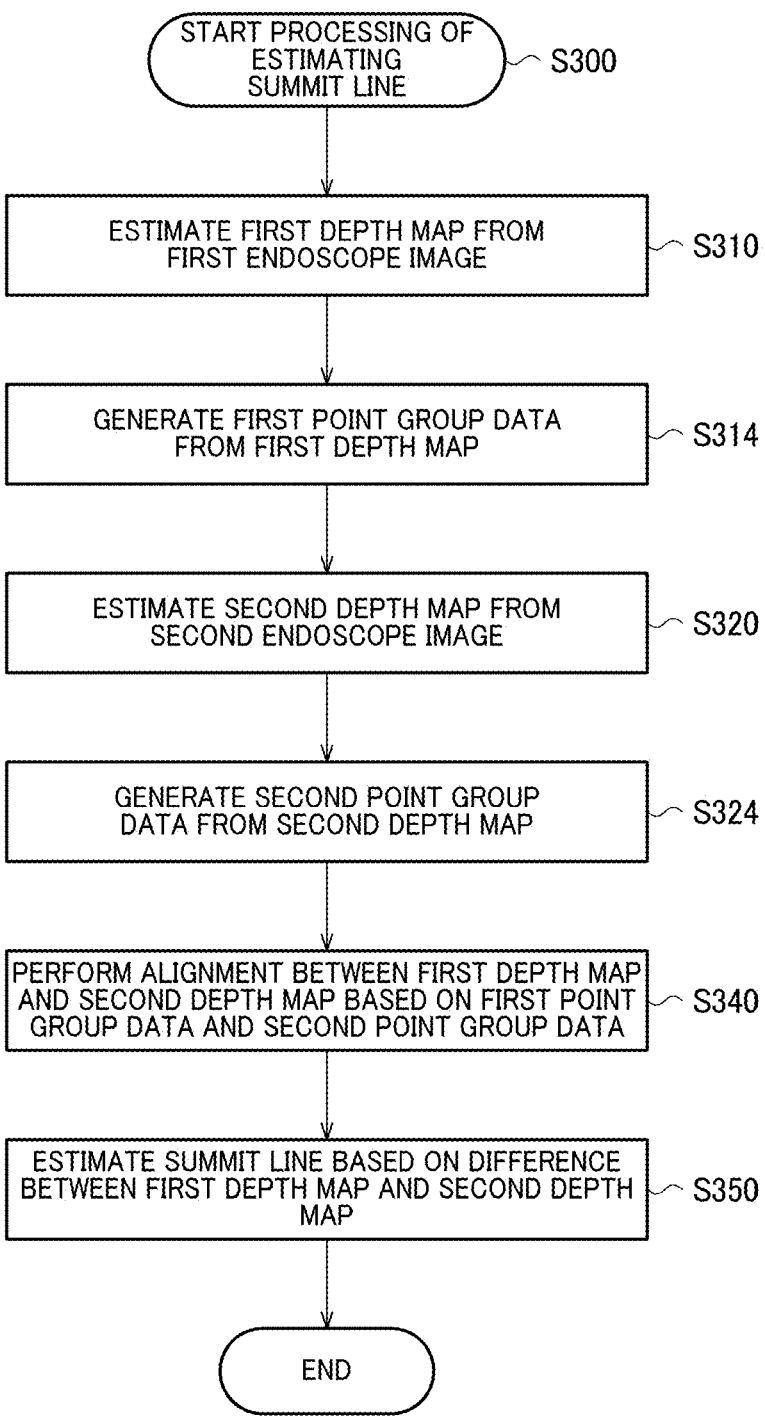
Figure 24:
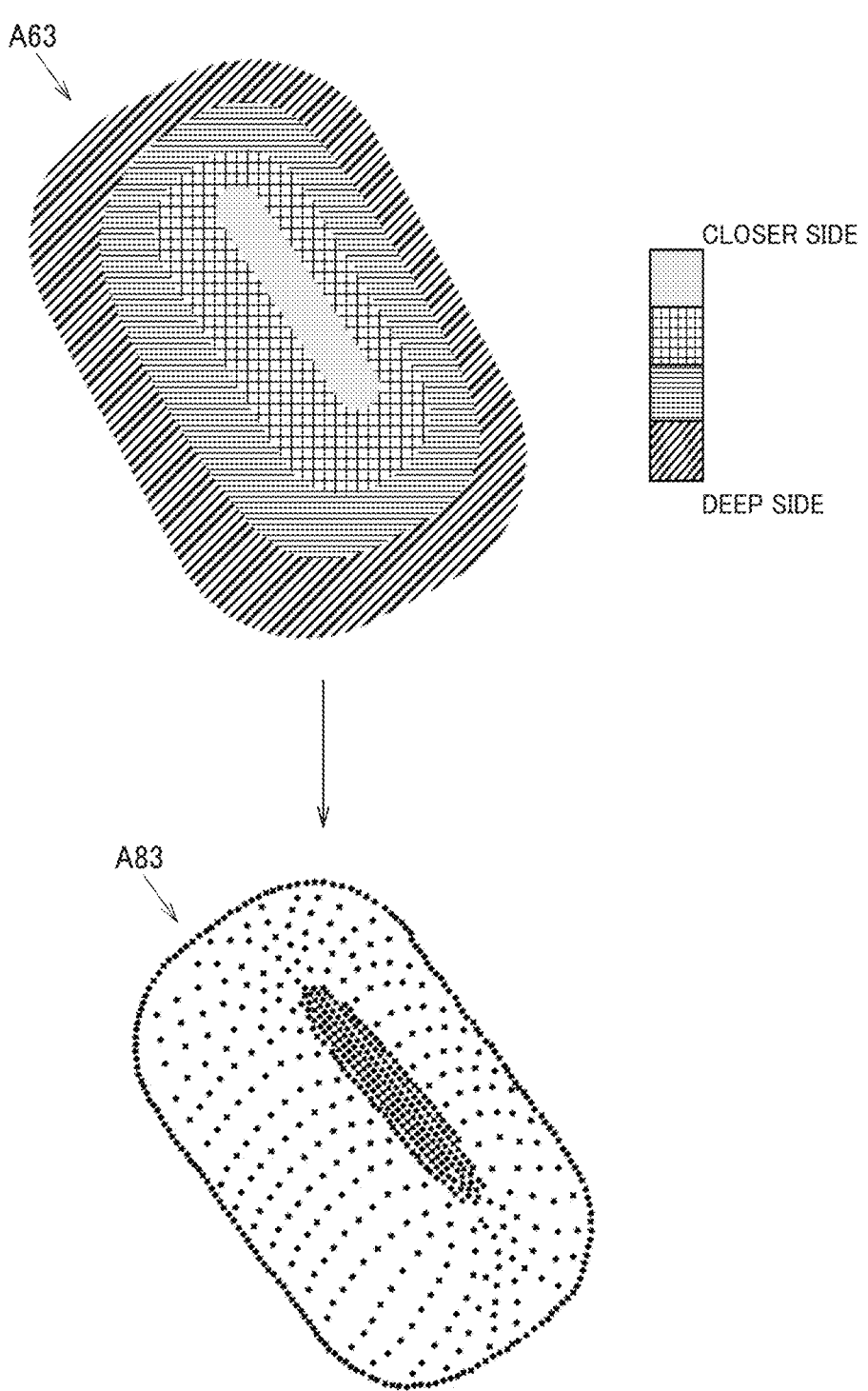
Figure 25:
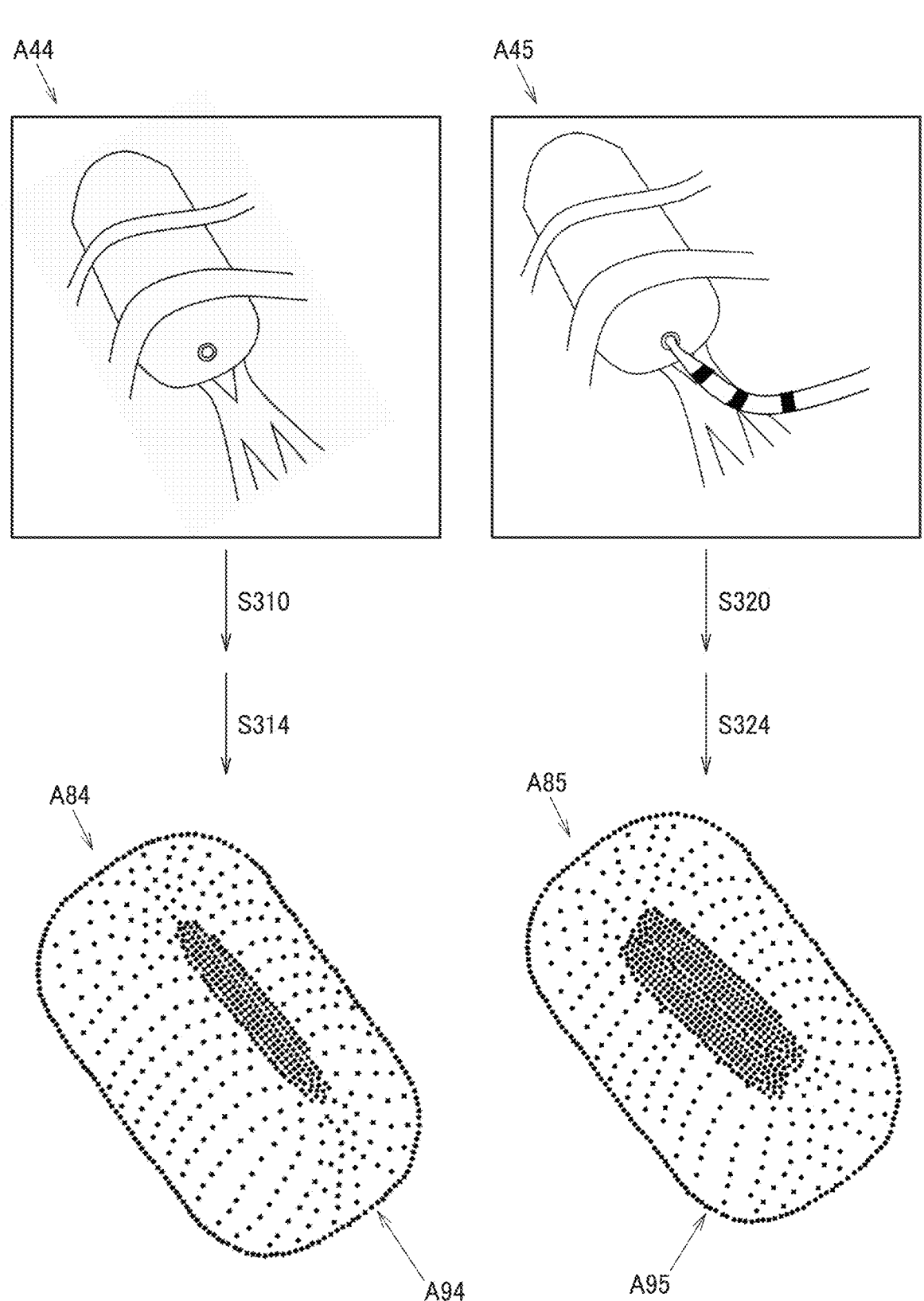
Figure 26:
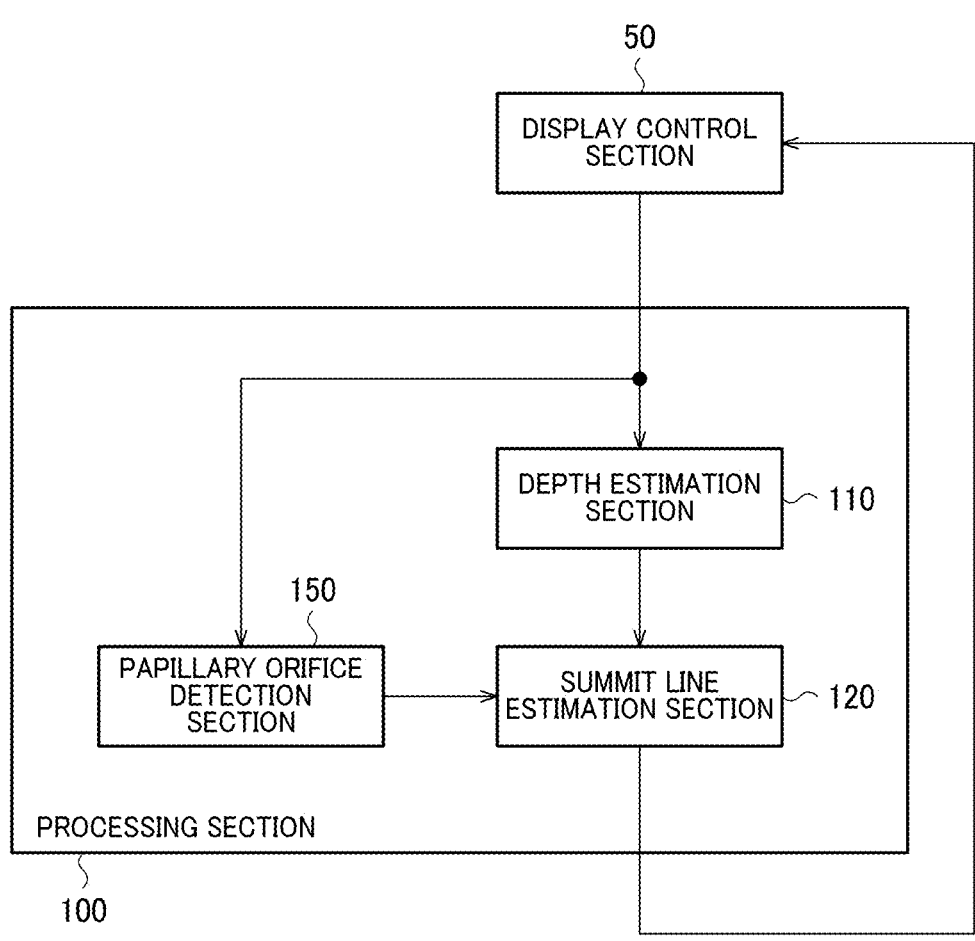
Figure 27:
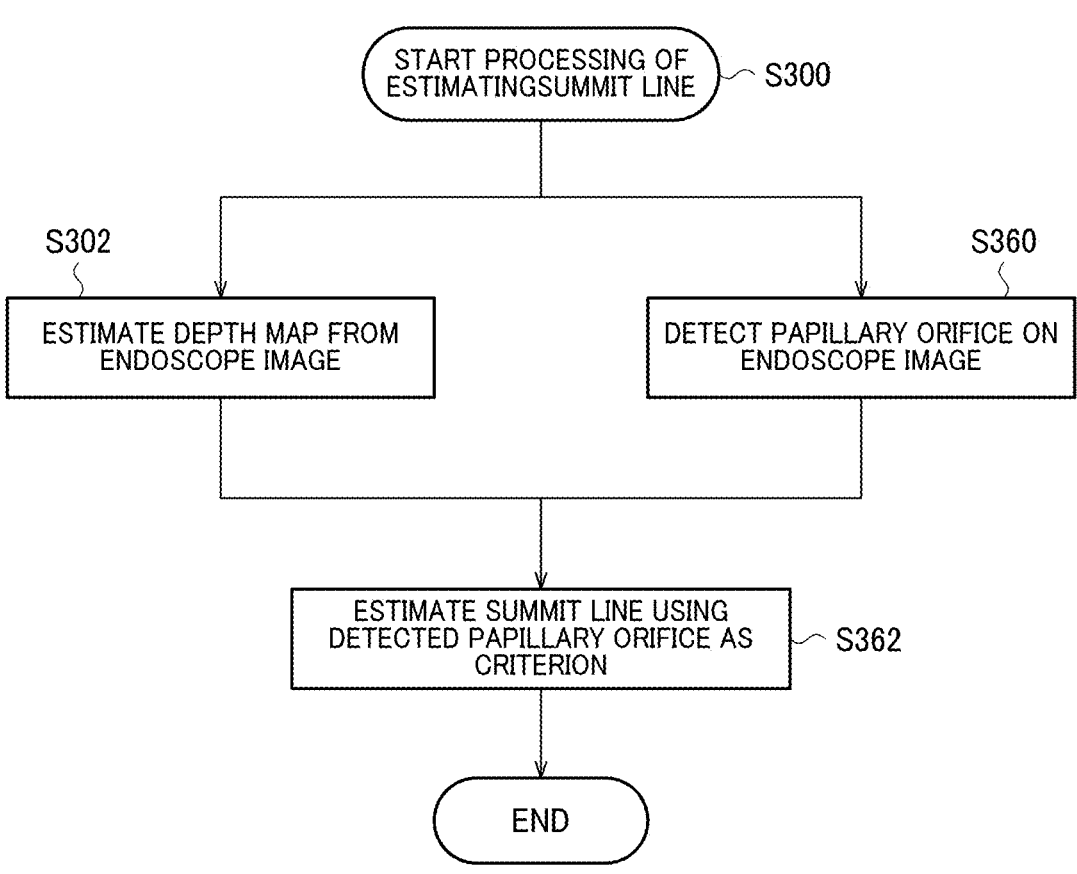
Figure 28:
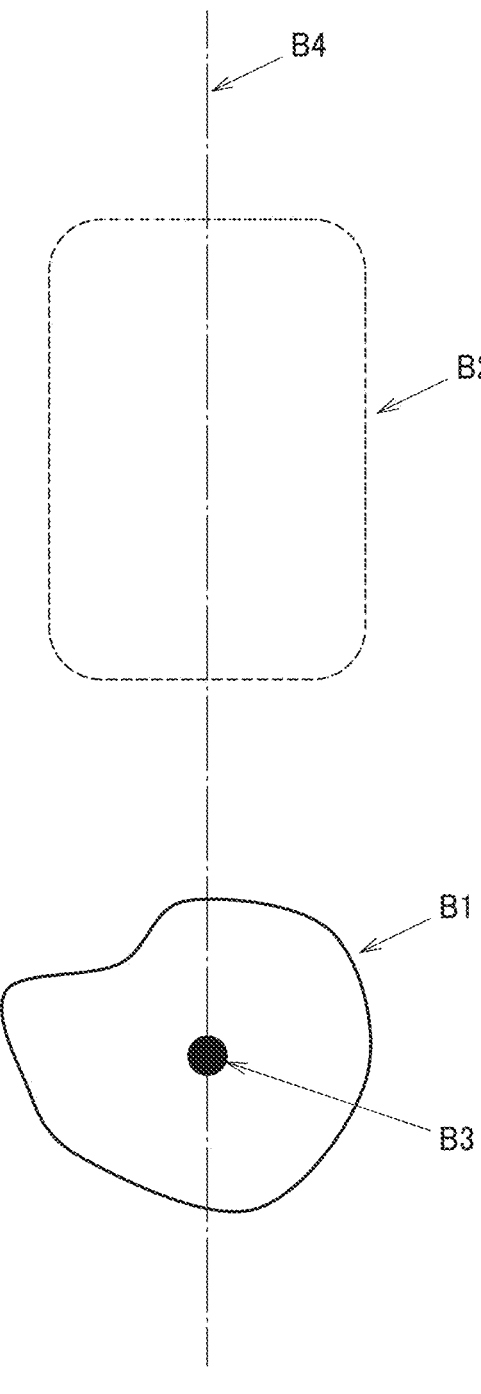
Figure 29:
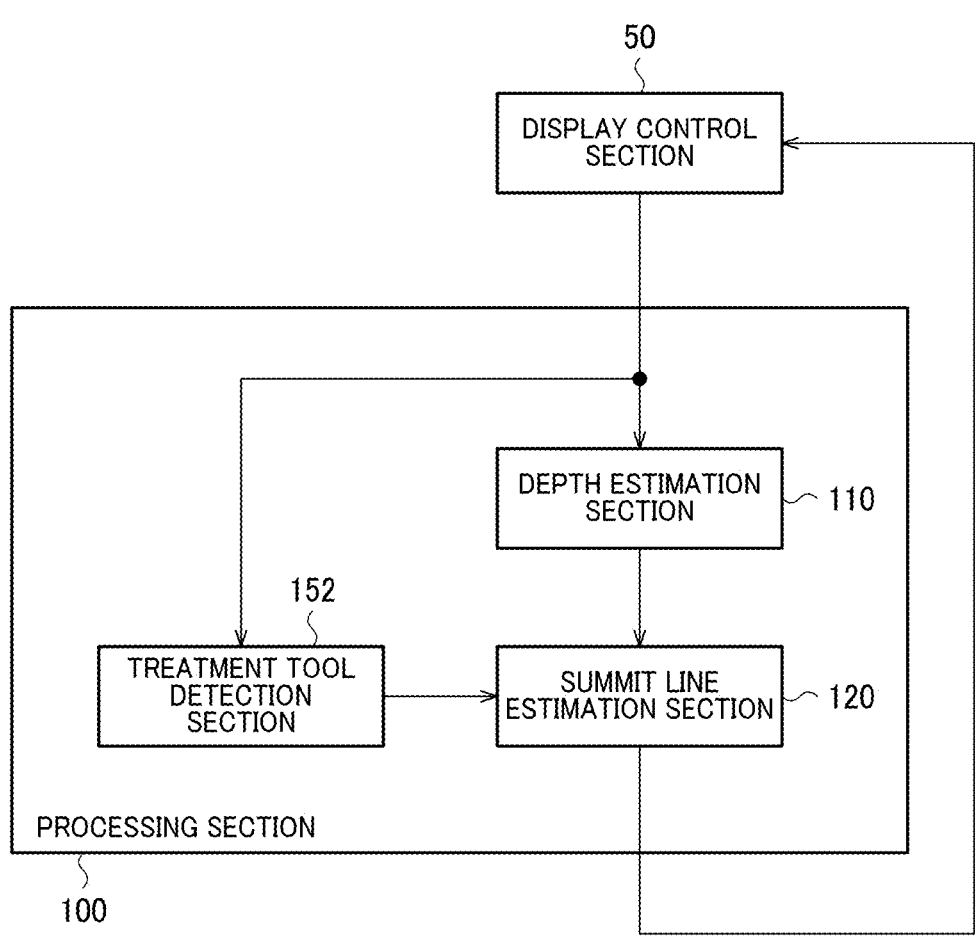
Figure 30:
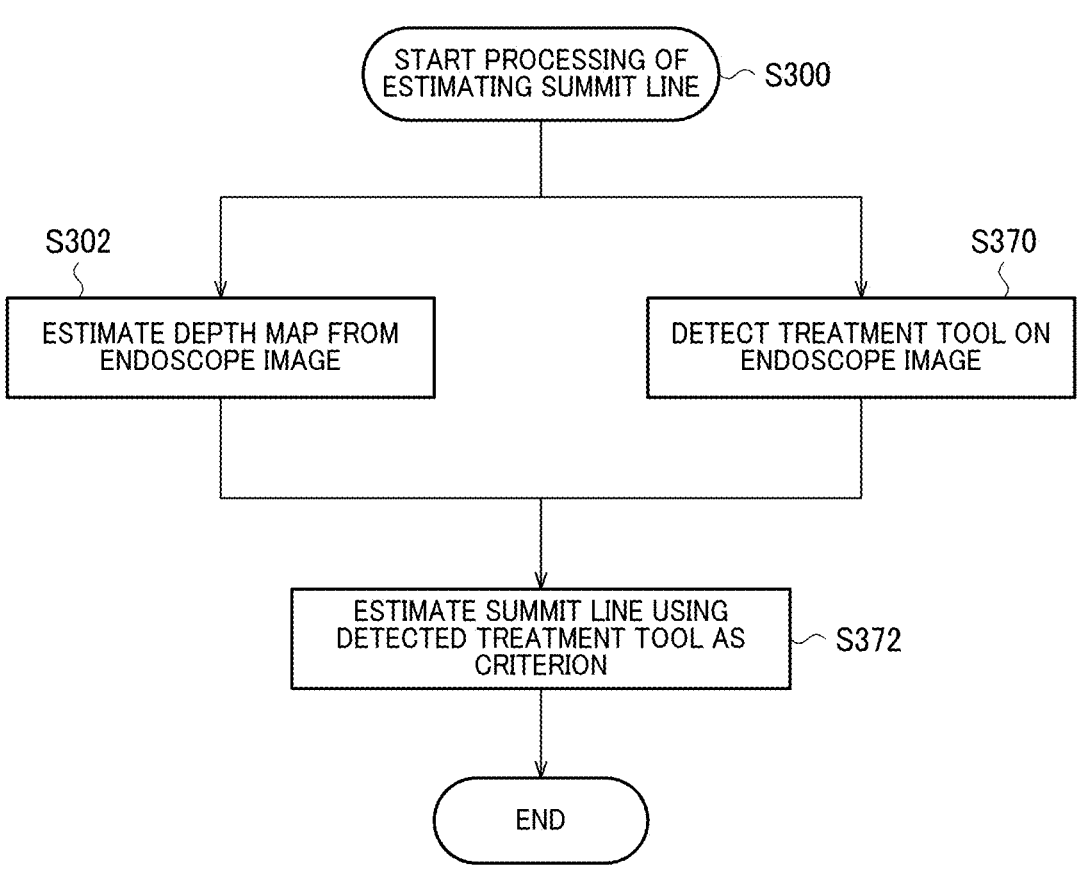
Figure 31:
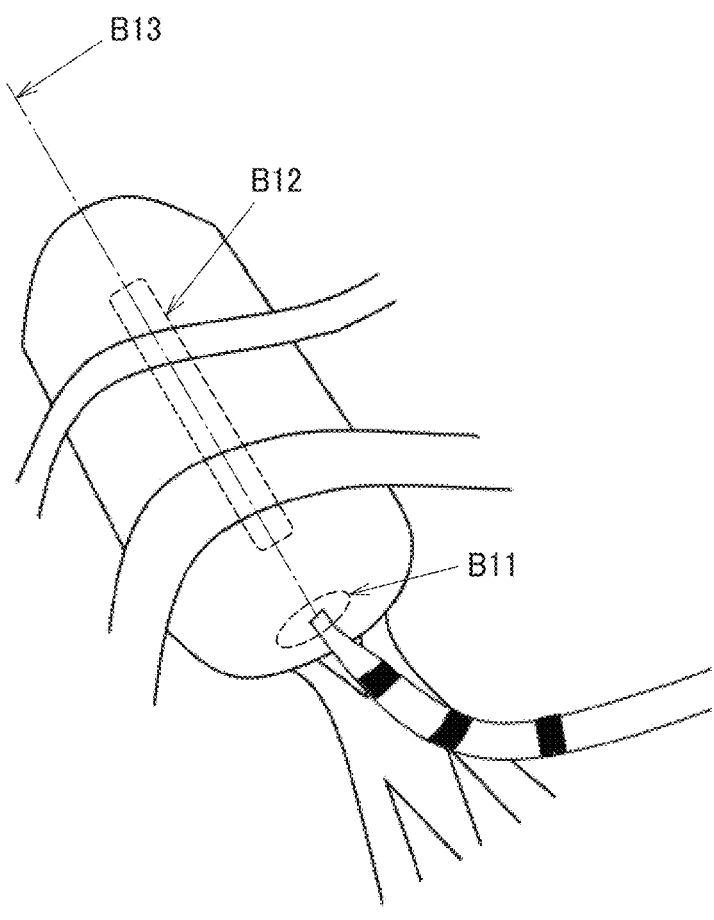
Figure 32:
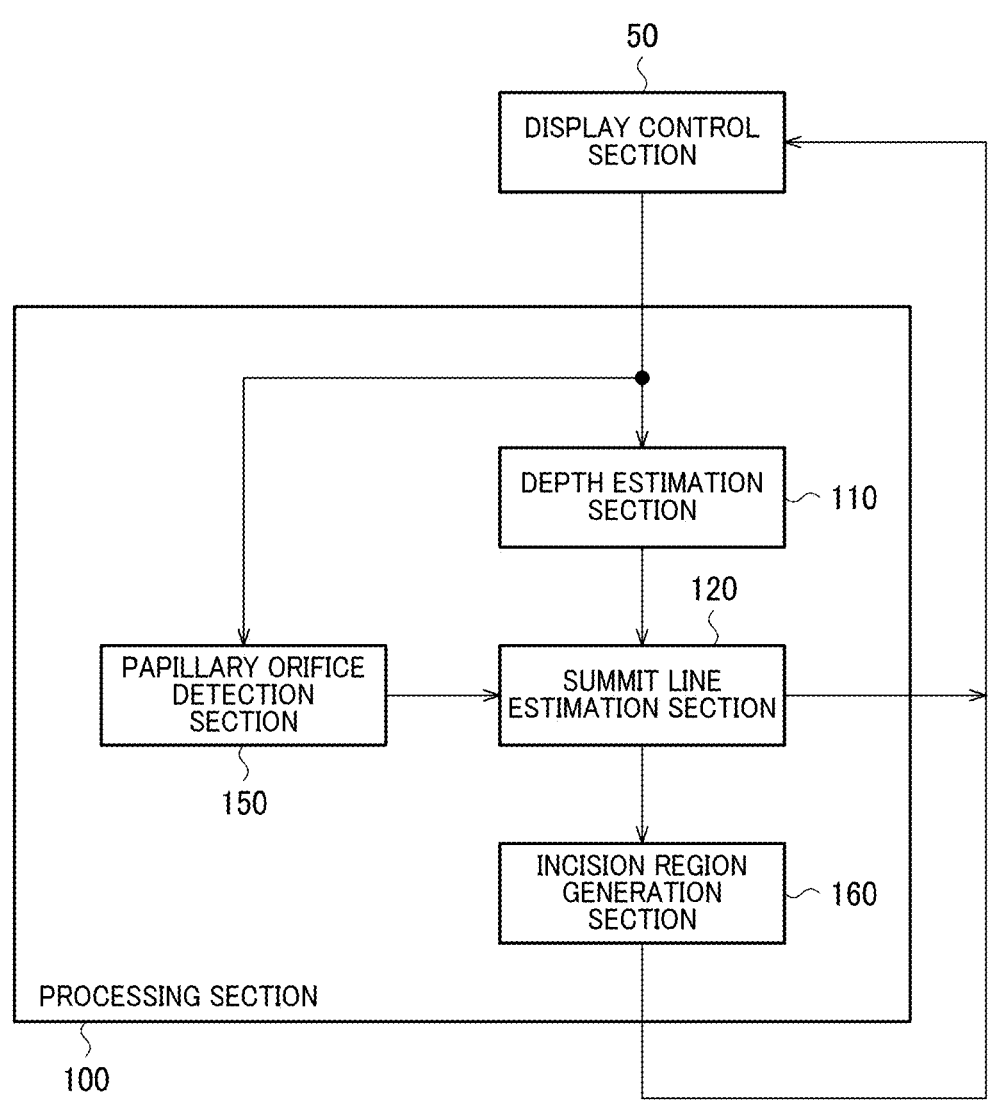
Figure 33:
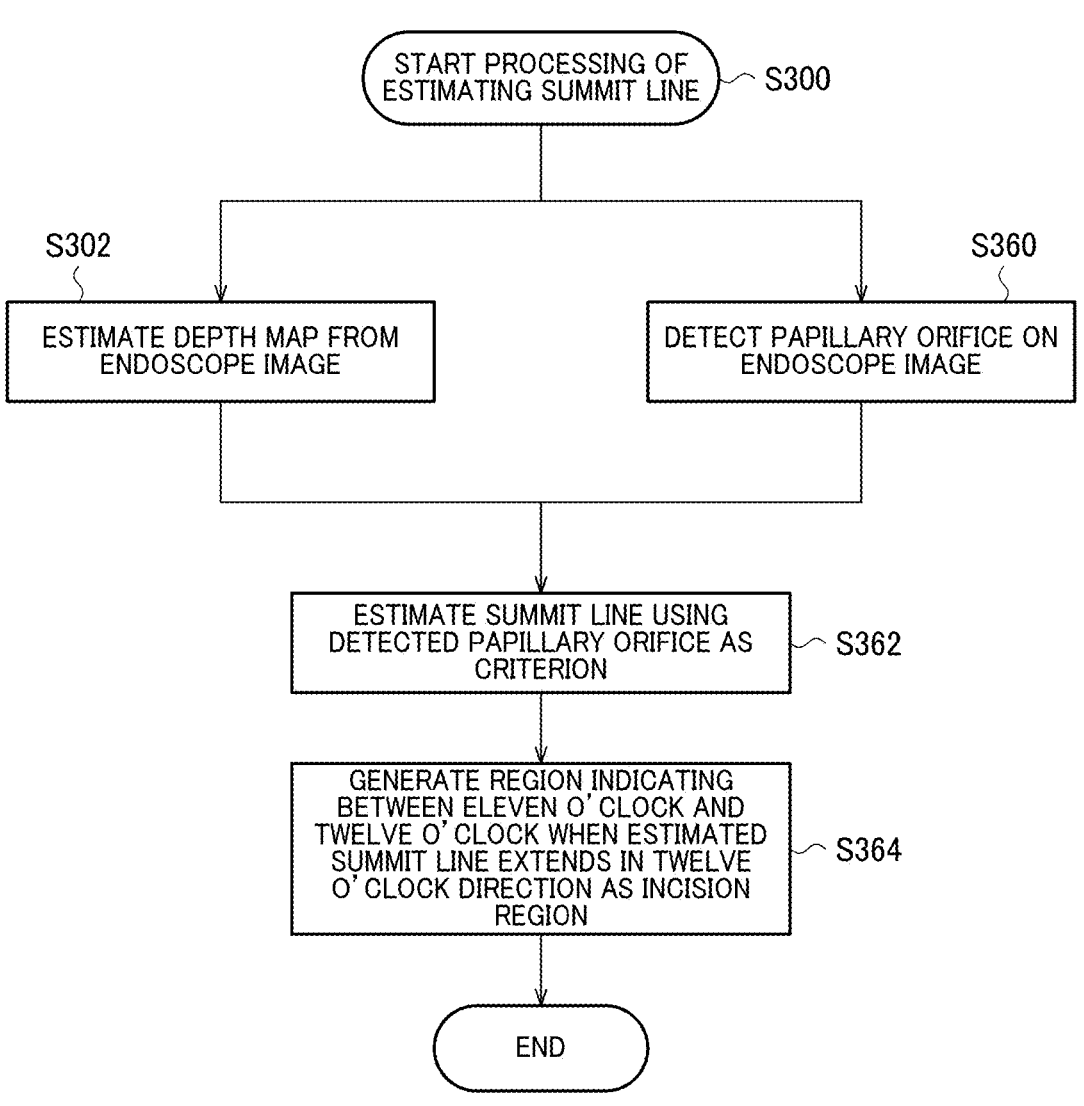
Figure 34:
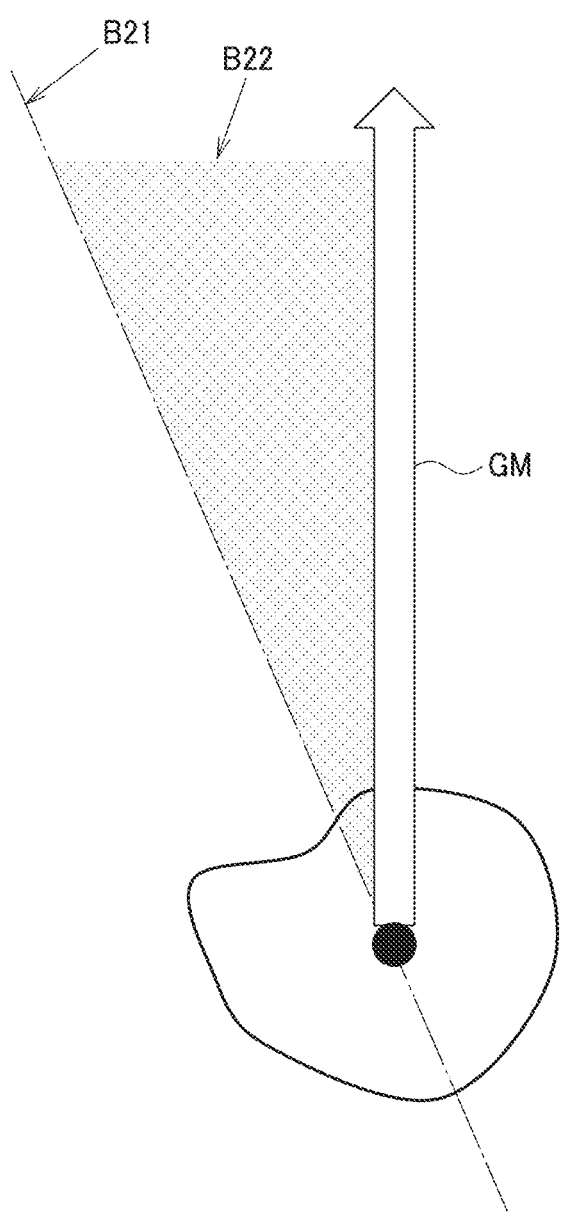
Figure 35:
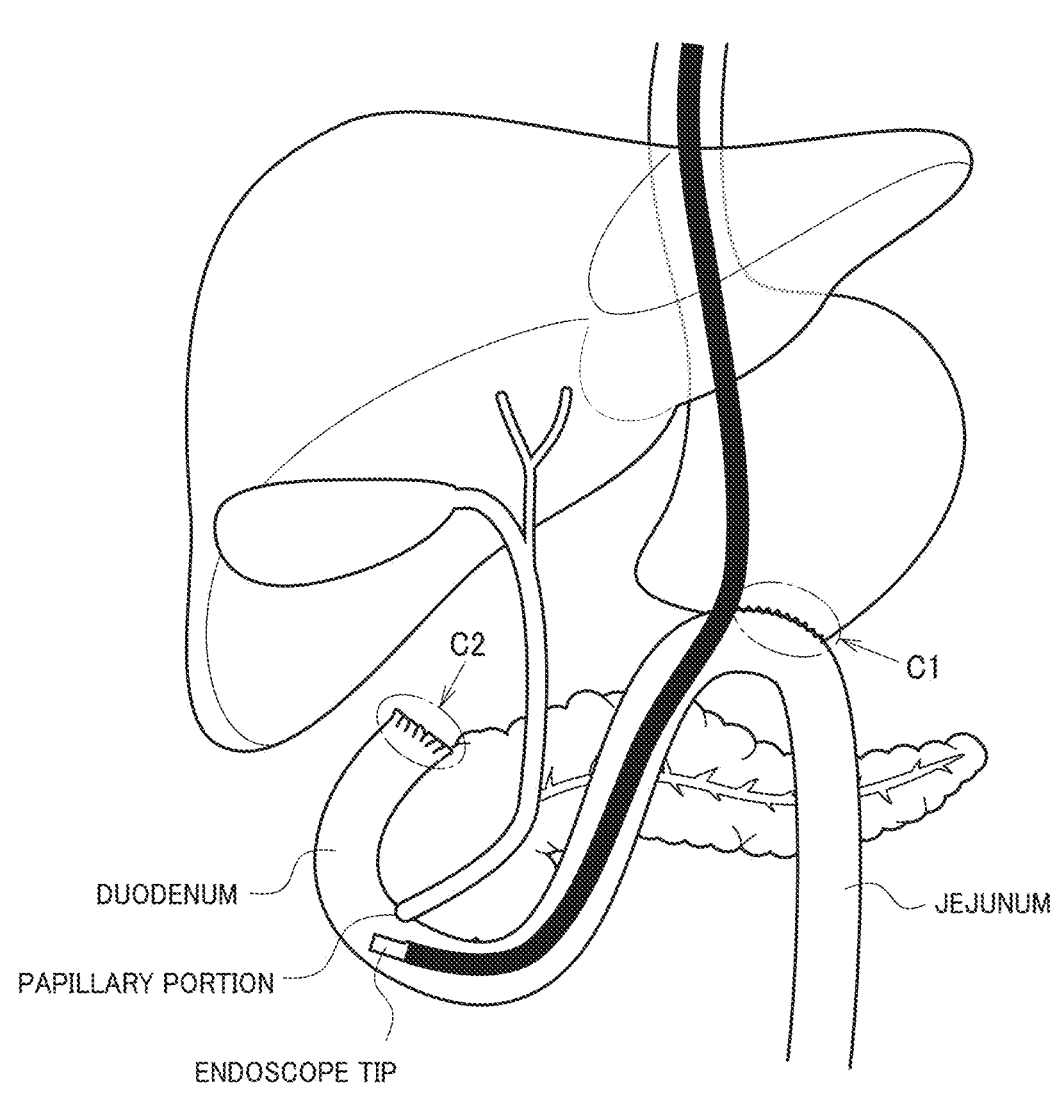
Figure 36:
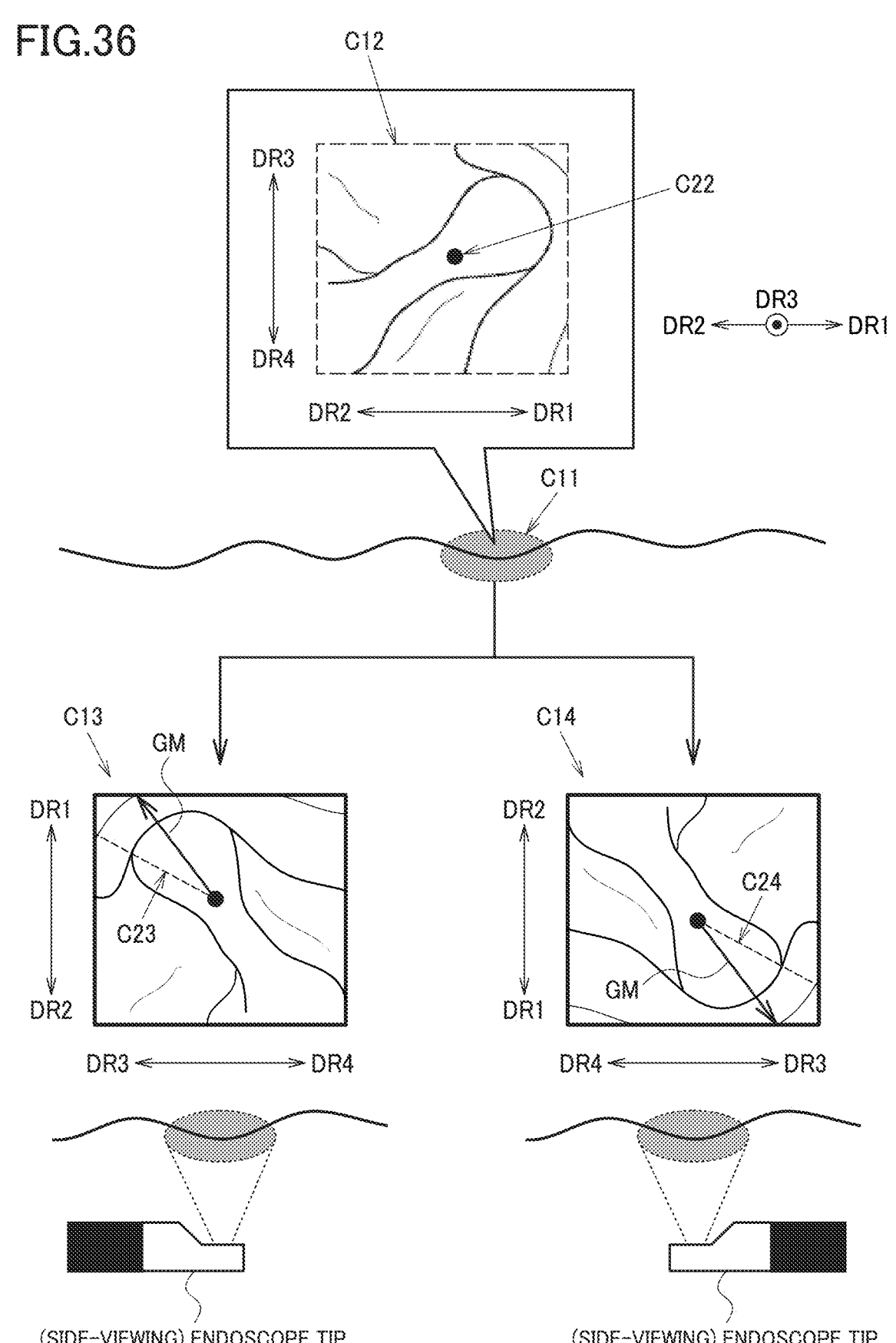
Figure 37:
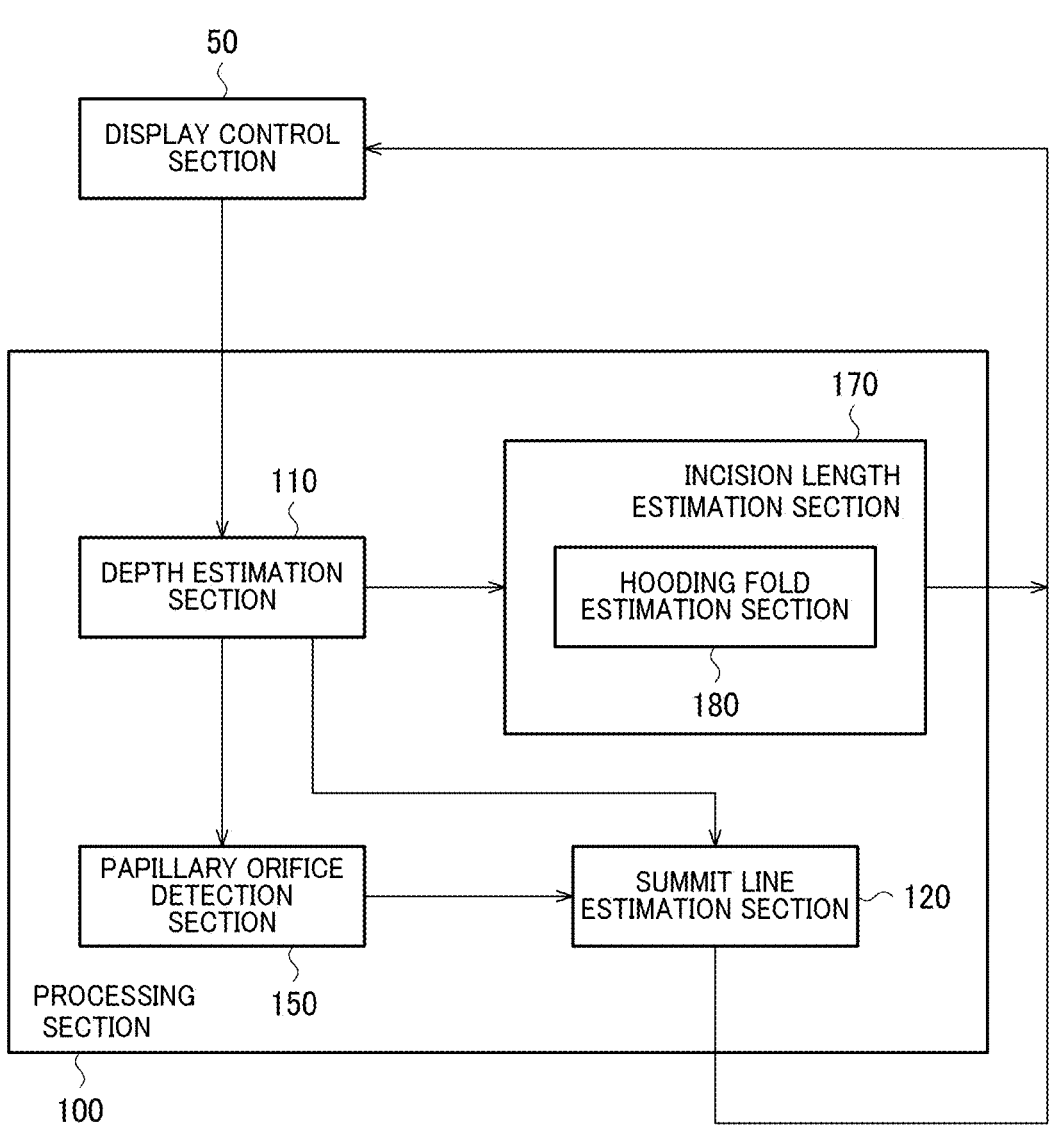
Figure 38:
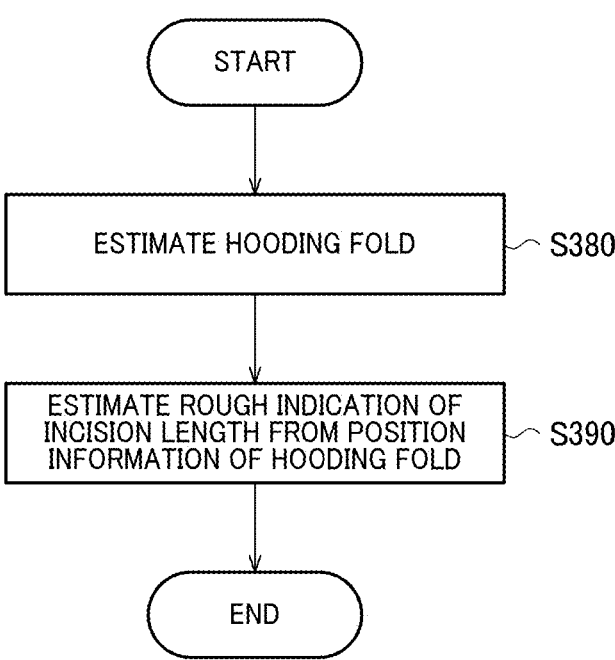
Figure 39:
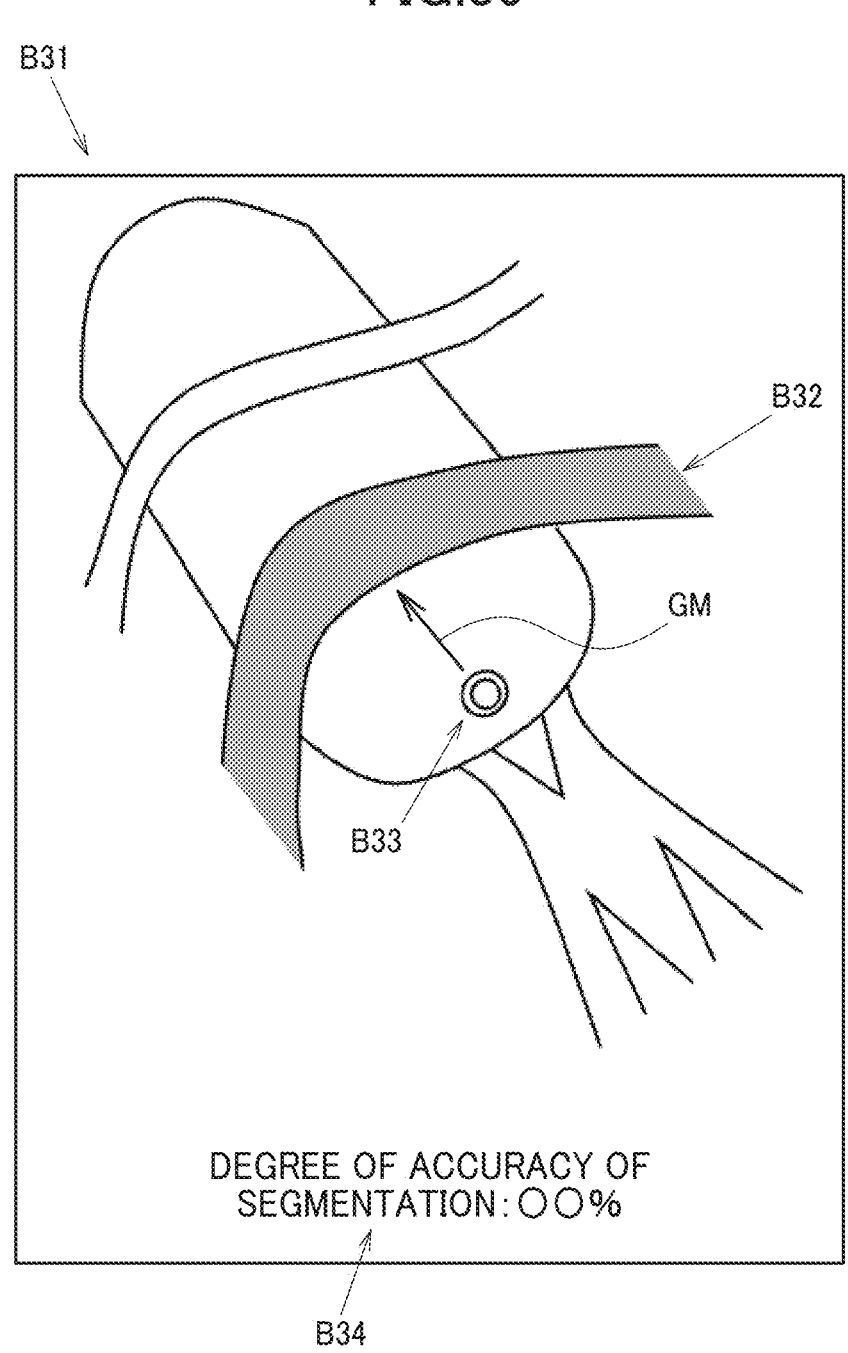

FIG. 7 is a view for describing a direction in which incision should be performed in the EST.
FIG. 8 is a flowchart describing a processing example in accordance with the present embodiment.
FIG. 9 is a flowchart describing a processing example of processing of estimating a summit line.
FIG. 10 is a diagram for describing a configuration example of a processing section.
FIG. 11 is a diagram for describing another configuration example of the processing system.
FIG. 12 is a view for describing estimation of the summit line.
FIG. 13 is a view for describing actions and effects of a method in accordance with the present embodiment.
FIG. 14 is a diagram for describing another configuration example of the processing system and the like.
FIG. 15 is a flowchart describing a processing example of processing performed by a pressure determination section.
FIG. 16 is a diagram for describing another configuration example of the processing section.
FIG. 17 is a flowchart describing a processing example of processing of acquiring an endoscope image.
FIG. 18 is a flowchart describing another processing example of the processing of estimating the summit line.
FIG. 19 is a view for describing a first depth map and a second depth map.
FIG. 20 is a diagram for describing another configuration example of the processing section.
FIG. 21 is a flowchart describing another processing example of the processing of estimating the summit line.
FIG. 22 is a diagram for describing another configuration example of the processing section.
FIG. 23 is a flowchart describing another processing example of the processing of estimating the summit line.
FIG. 24 is a view for describing generation of point group data.
FIG. 25 is a view for describing first point group data and second point group data.
FIG. 26 is a diagram for describing another configuration example of the processing section.
FIG. 27 is a flowchart describing another processing example of the processing of estimating the summit line.
FIG. 28 is a view for describing a summit line that starts from the papillary orifice.
FIG. 29 is a diagram for describing another configuration example of the processing section.
FIG. 30 is a flowchart describing another processing example of the processing of estimating the summit line.
FIG. 31 is a view for describing a summit line that starts from one end of a treatment tool.
FIG. 32 is a diagram for describing another configuration example of the processing section.
FIG. 33 is a flowchart describing another processing example of the processing of estimating the summit line.
FIG. 34 is a view for describing an incision region.
FIG. 35 is a view for describing an example in which a structure of organs is changed.
FIG. 36 is a view for describing a relationship between the structure of organs and display of the incision region.
FIG. 37 is a diagram for describing another configuration example of the processing section.
FIG. 38 is a flowchart describing a processing example of processing performed by an incision length estimation section.
FIG. 39 is a view for describing actions and effects of processing performed by the incision length estimation section.

Figure 40:
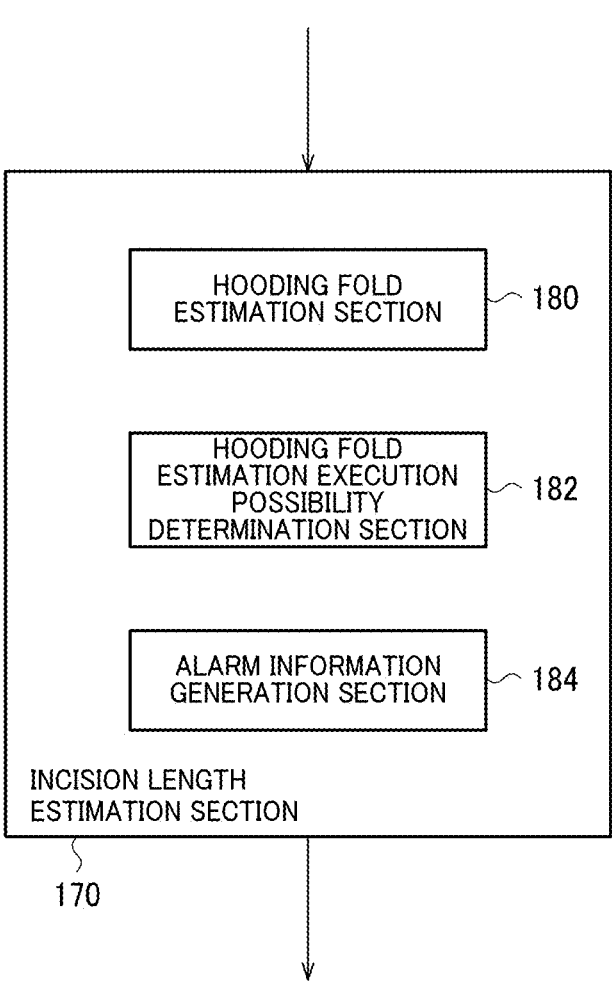

FIG. 40 is a diagram for describing another configuration example of the incision length estimation section.

Figure 41:
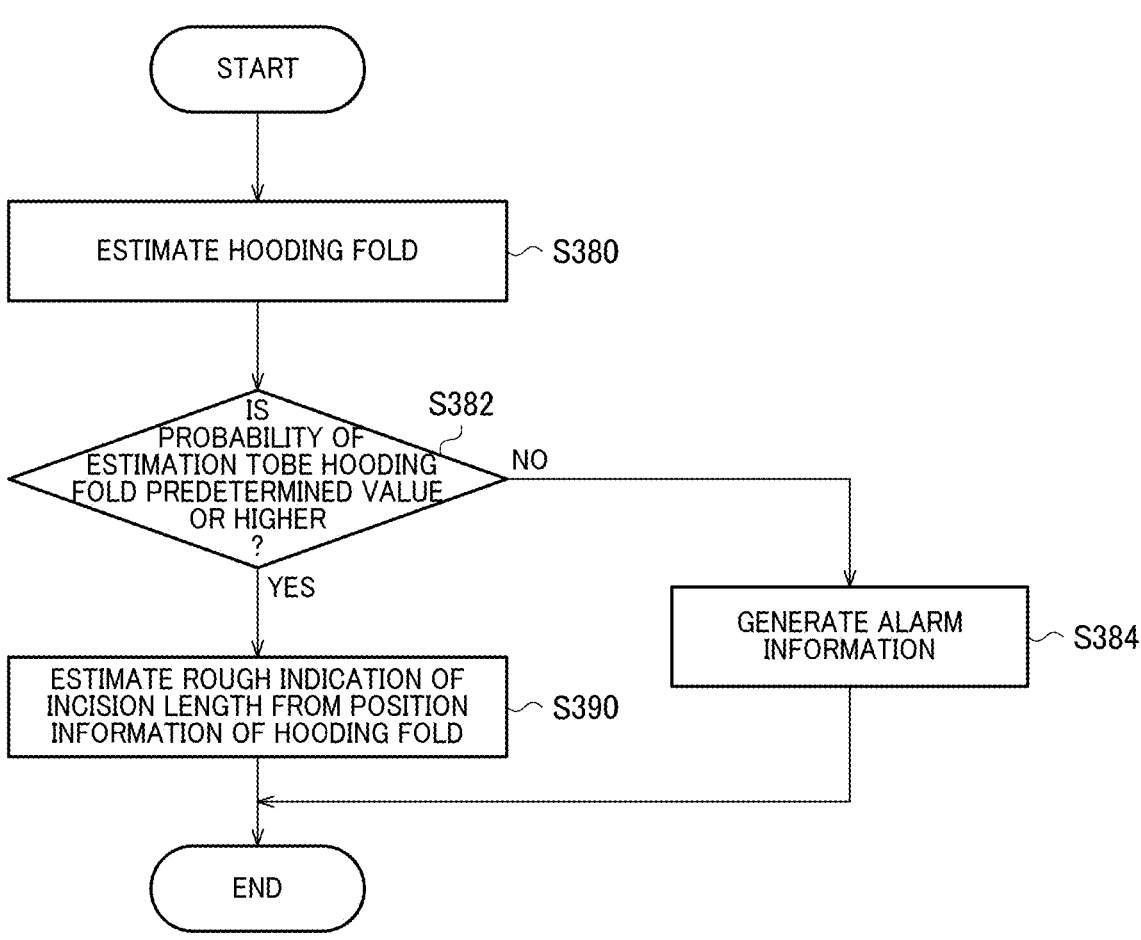

FIG. 41 is a flowchart describing another processing example of the processing performed by the incision length estimation section.

Figure 42:
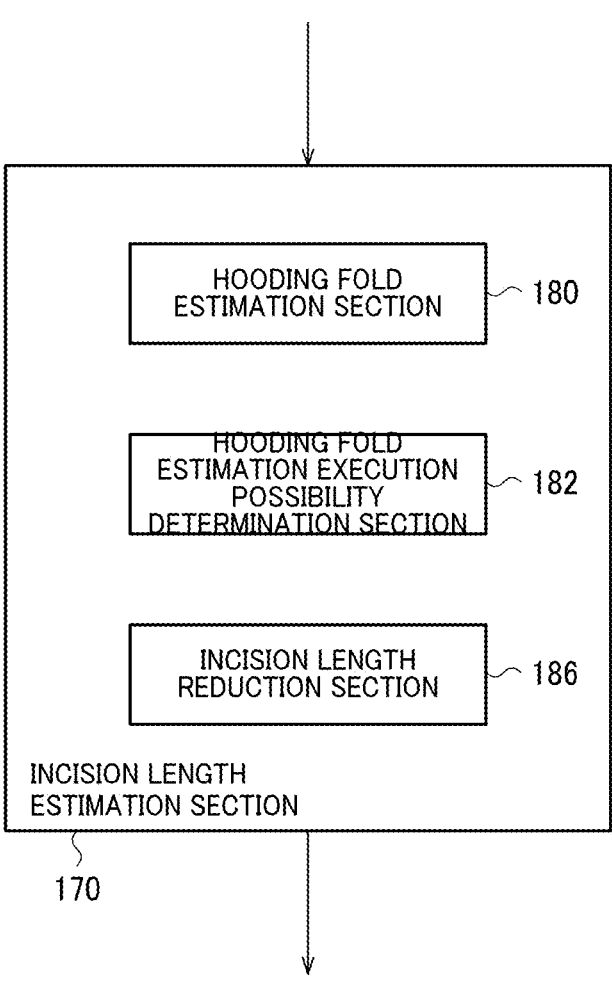

FIG. 42 is a diagram for describing another configuration example of the incision length estimation section.

Figure 43:
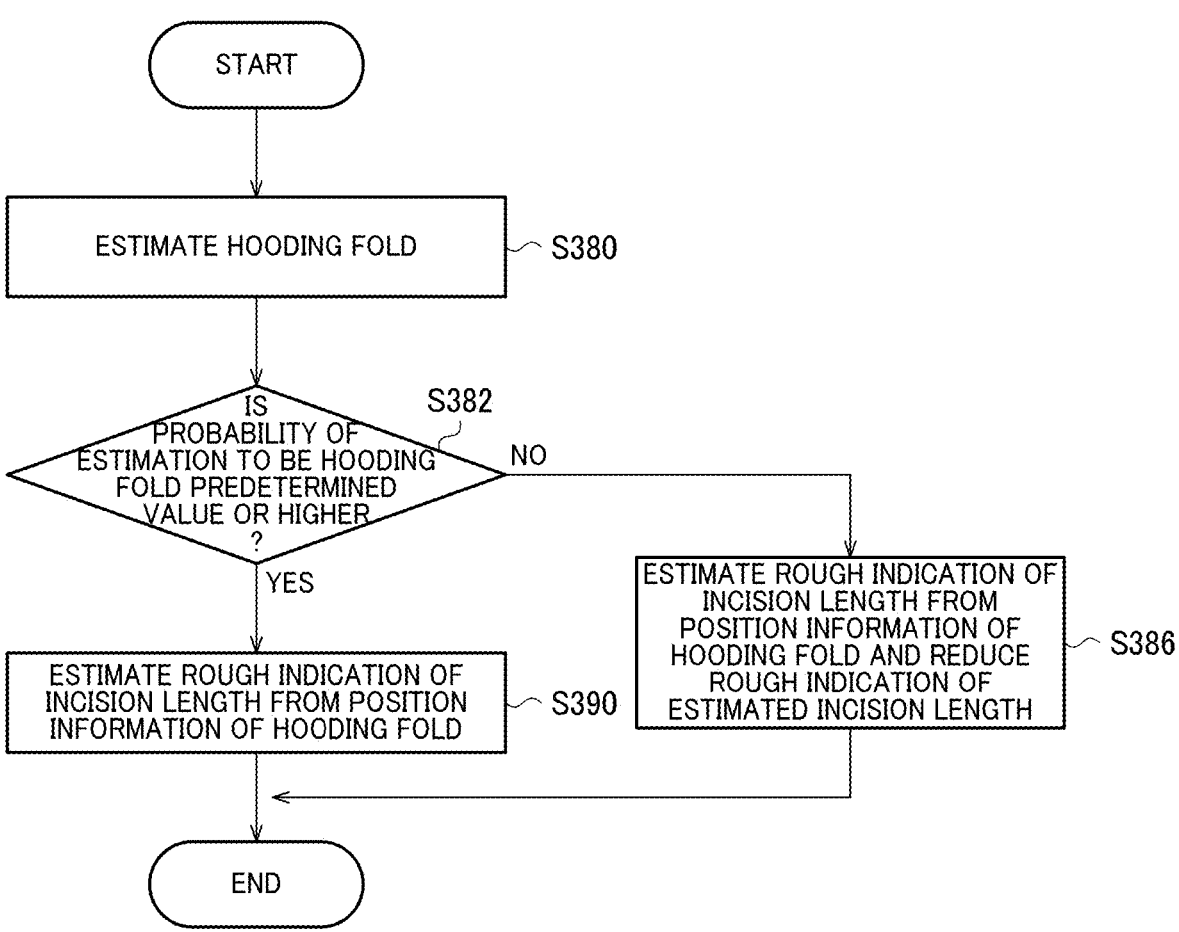

FIG. 43 is a flowchart describing another processing example of the processing performed by the incision length estimation section.

Figure 44:
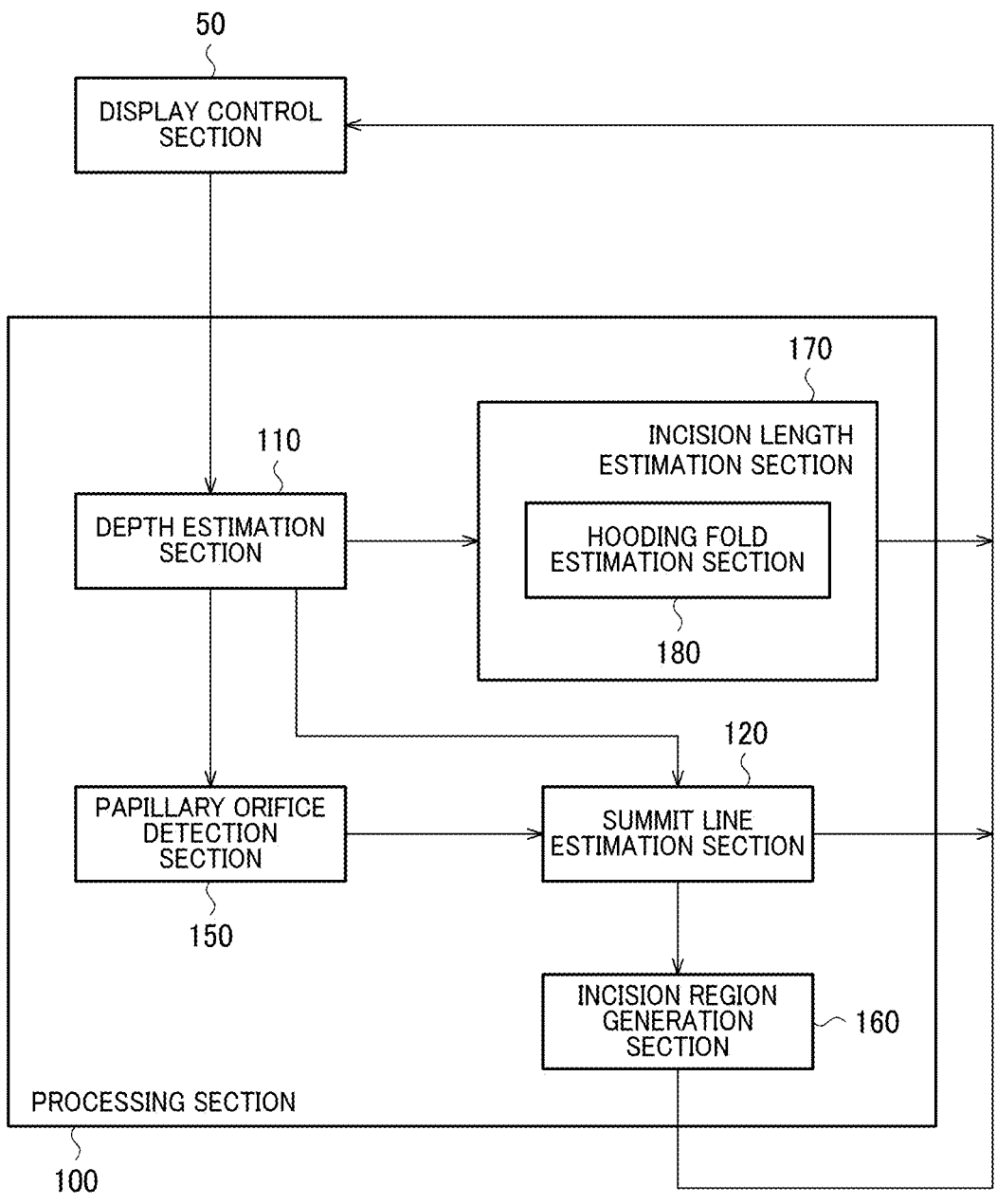

FIG. 44 is a diagram for describing another configuration example of the processing section.

DETAILED DESCRIPTION

The following disclosure provides many different embodiments, or examples, for implementing different features of the provided subject matter. These are, of course, merely examples and are not intended to be limiting. In addition, the disclosure may repeat reference numerals and/ or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Figure 1:
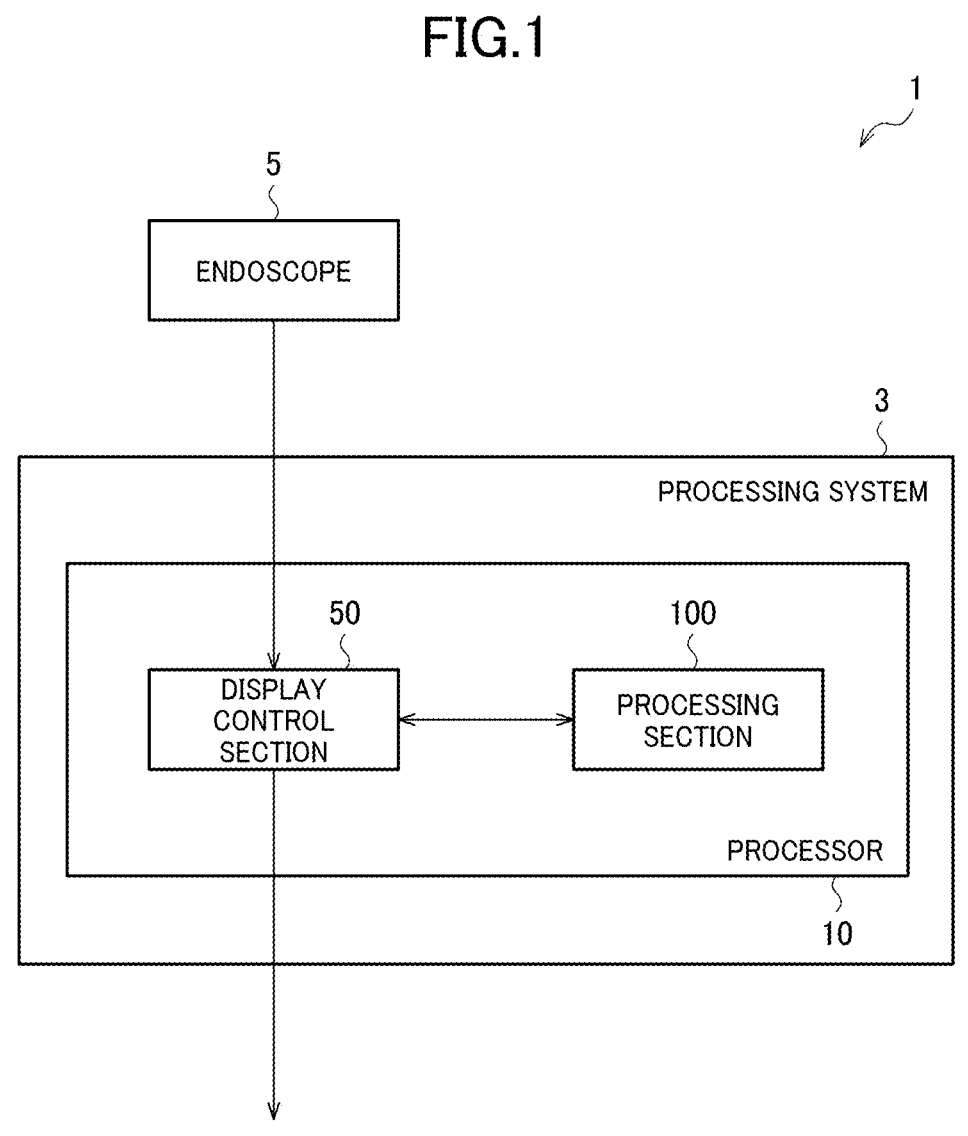

FIG. 1 is a block diagram for describing a configuration example of an endoscope system 1 in accordance with the present embodiment and a processing system 3 included in the endoscope system 1. The processing system 3 in accordance with the present embodiment includes a processor 10. The processor 10 in accordance with the present embodiment has the following hardware configuration. The hardware can include at least one of a circuit that processes a digital signal or a circuit that processes an analog signal. For example, the hardware can include one or more circuit devices mounted on a circuit board, or one or more circuit elements. The one or more circuit device are, for example, integrated circuits (ICs) or the like. The one or more circuit elements are, for example, resistors, capacitors, or the like.

For example, the processing system 3 in accordance with the present embodiment may have a configuration including a memory 20, which is not illustrated in FIG. 1, and the processor 10 that operates based on information stored in the memory 20. With this configuration, the processor 10 can function as a display control section 50, a processing section 100, and the like. The information is, for example, a program, various kinds of data, and the like. Note that the program may include, for example, a trained model 22, which will be described later with reference to FIG. 11. A central processing unit (CPU), a graphics processing unit (GPU), a digital signal processor (DSP), or the like can be used as the processor 10. The memory 20 may be a semiconductor memory such as a static random access memory (SRAM) and a dynamic random access memory (DRAM). The memory 20 may be a register. The memory 20 may be a magnetic storage device such as a hard disk device. The memory 20 may be an optical storage device such as an optical disk device. For example, the memory 20 stores a computer-readable instruction. The instruction is executed by the processor 10, whereby a function of each section is implemented as processing. The instruction mentioned herein may be an instruction set that is included in the program, or may be an instruction that instructs the hardware circuit included in the processor 10 to operate. The memory 20 is also referred to as a storage device. A main section that performs processing or the like regarding the method in accordance with the present embodiment is collectively referred to as the processor 10 for explanatory convenience unless otherwise described, but may be read as the processing section 100 serving as software or the like as appropriate. In addition, FIG. 1 illustrates the processing system 3 so as to include one processor 10, which does not prevent implementation of the method in accordance with the present embodiment by a plurality of processors 10. That is, the display control section 50 and the processing section 100 may be configured as individual processors 10. The same applies to each section included in the processing section 100. For example, a depth estimation section 110 and a summit line estimation section 120, which will be described later with reference to FIG. 10, may be implemented as individual processors 10. The same applies to FIGS. 14, 16, 20, 22, 26, 29, 32, 37, 40, 42, and 44.

The display control section 50 receives an image signal from an imager, which is arranged in a tip portion of an endoscope 5 and not illustrated, and performs processing of generating a display image from the image signal and displaying the display image on a display device 9, which is not illustrated in FIG. 1. In the present embodiment, an image captured by the imager, which is arranged in the tip portion of the endoscope 5 and not illustrated, is referred to as an endoscope image. The endoscope image may be a still image converted from a video image captured by the camera. In the present embodiment, the imaging device captures an image of the duodenal papilla including the oral protrusion, which will be described later with reference to FIG. 2. That is, the processor 10 in accordance with the present embodiment functions as the display control section 50, and acquires an endoscope image in which the duodenal papilla including the oral protrusion is imaged. Although details will be described later, the duodenal papilla is a portion including the papillary orifice and a surrounding structure of the papillary orifice in the duodenum. The surrounding structure mentioned herein is, for example, the oral protrusion, the hooding fold, the circular fold, the frenum, and the like. In the present embodiment, the endoscope image in which the duodenal papilla including the oral protrusion is imaged is an endoscope image in which at least the oral protrusion among the above-mentioned surrounding structure is seen.

The processing section 100 controls each section of the processing system 3. Although details will be described later, the processing section 100 functions as each section that executes processing regarding the method in accordance with the present embodiment. For example, the processing section 100 receives display image data generated by the display control section 50, causes each section included in the processing section 100 to generate various kinds of data, and transmits the various kinds of generated data to the display control section 50. With this configuration, the display control section 50 controls the display device 9 based on the image data captured by the imager and the various kinds of data received from the processing section 100. Whit this configuration, display on the display device 9 is implemented so that the endoscope image and a guide display GM or the like are superimposed on each other. The guide display GM will be described later. Each section included in the processing section 100 is, for example, the summit line estimation section 120, an incision region generation section 160, an incision length estimation section 170, and the like.

The endoscope 5 is, for example, a medical flexible endoscope. As described later, the present embodiment relates to a method of displaying the guide display GM when EST is performed after ERCP is performed. As the endoscope 5 in this case, although not illustrated in detail, mainly used is a side-viewing endoscope provided with an objective lens of the imager, an illumination lens, and an opening of a treatment tool channel on a side surface in the endoscope tip portion. Note that the ERCP is an abbreviation for endoscopic retrograde cholangio pancreatography, and the EST is an abbreviation for endoscopic sphincterotomy.

Figure 2:
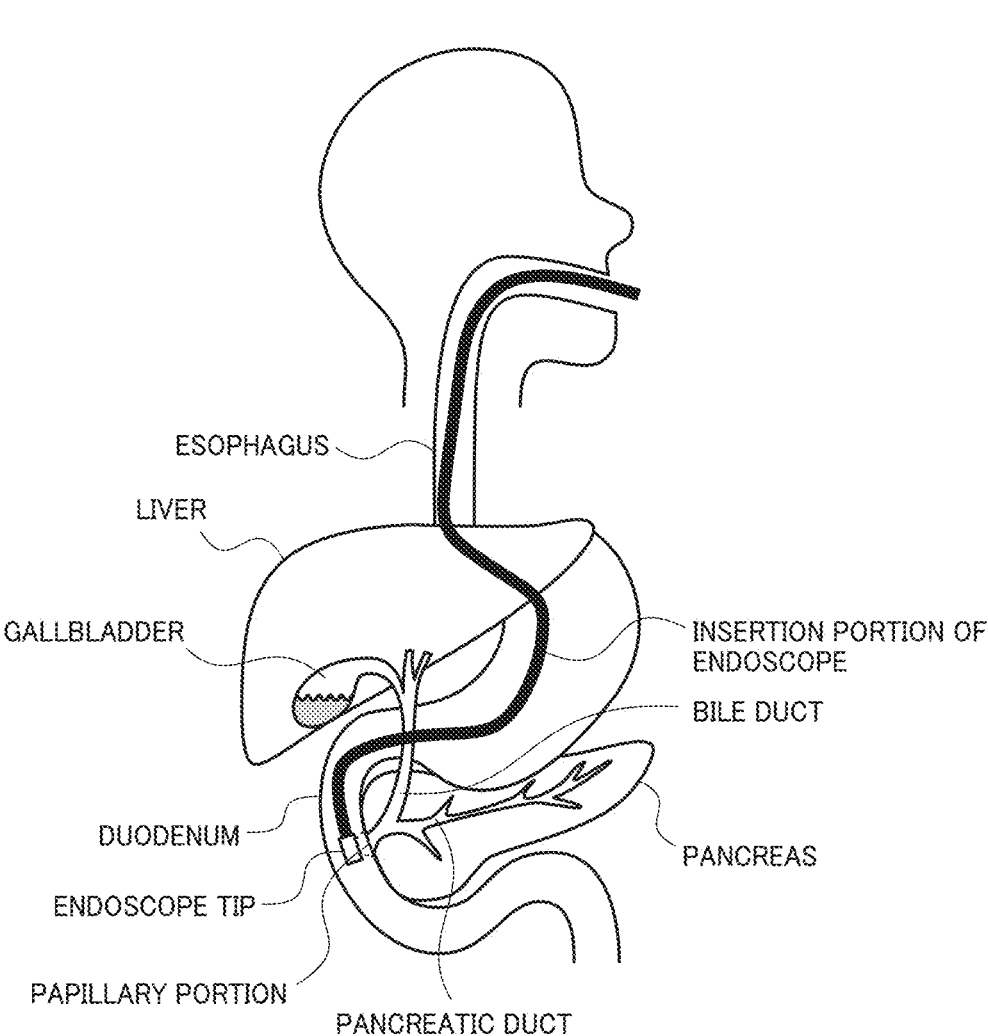
FIG. 2 is a view illustrating organs and tissues that are related to a treatment such as endoscopic sphincterotomy (EST).

FIG. 2 illustrates organs and tissues that are related to the above-mentioned manipulation. Note that an organ has a unique structure in which a plurality of types of tissues gathers together, and has a specific function. For example, in FIG. 2, the liver, the gallbladder, the pancreas, the esophagus, the stomach, and the duodenum correspond to the organs. The tissues are formed by related cells being coupled to each other, such as blood vessels, muscles, and skin. For example, in FIG. 2, the bile duct and the pancreatic duct correspond to the tissues. Note that an example of a structure of the organs illustrated in FIG. 2 represents a general example in which the organs are not changed by a surgical treatment or the like, which will be described later with reference to FIG. 35. The structure of the organs can also be called an anatomical structure of the digestive tract. Note that the digestive tract mentioned herein is the stomach and the intestinal tract. The stomach mentioned herein includes a remnant stomach in a case where gastric resection is performed. The intestinal tract includes the small intestine, the large intestine, and the like. The small intestine includes the duodenum, the jejunum, and the ileum. In a case of the structure of the organs illustrated in FIG. 2, the endoscope tip portion is inserted from the stomach side toward the duodenum in the ERCP manipulation.

An insertion portion is then inserted until a position at which the papillary portion is roughly seen in the imager of the endoscope 5, and the endoscope 5 is aligned with the duodenal papilla. Specifically, for example, the position of the endoscope tip portion is adjusted so that the objective lens of the imager of the endoscope 5 directly faces the duodenal papilla and the duodenal papilla is located at the center of an imaging region of the imager.

FIG. 3 is a view schematically illustrating a form of the duodenal papilla when the duodenal papilla is viewed from a directly facing position. Structures called the oral protrusion, the hooding fold, the circular fold, and the frenum exist in the periphery of the papillary orifice, as illustrated in FIG. 3. The oral protrusion is a protrusion extending in a ridge shape from the papillary orifice. Note that directions DR11, DR12, and DR13 are illustrated as directions mutually orthogonal for explanatory convenience in FIG. 3. In the present embodiment, one side toward the direction DR12 may be referred to as an "upper side". A right side surface of the duodenal papilla illustrated in FIG. 3 is as schematically illustrated in FIG. 4. In the following description, one side toward the direction DR13 may be referred to as a "deep side". Meanwhile, the opposite side of the one side toward the direction DR13, that is, an objective lens side of the imager of the endoscope 5 may be referred to as a "closer side".

In the ERCP, a cannula is inserted into the treatment tool channel, which is not illustrated, in the endoscope 5 to project the cannula from a channel opening in the endoscope tip portion, and a tip of the cannula is inserted into the bile duct via the papillary orifice. The cannula is a medical tube that is inserted into the body and used for a medical purpose. A contrast agent is injected into the cannula and is poured from the tip of the cannula into the bile duct. X-ray imaging or computed tomography (CT) imaging is performed in this state, whereby an X-ray image or a CT image, in which the bile duct, the gallbladder, and the pancreatic duct are seen, can be acquired. Thereafter, a guide wire is inserted into the cannula to project the guide wire from the tip of the cannula, and the guide wire is inserted into the bile duct. The cannula is then removed while the guide wire is placed and fixed inside the bile duct. This leads to a state where only the guide wire projects from the endoscope tip portion, which is not illustrated, and is placed and fixed inside the bile duct, as illustrated in FIG. 5. Note that although not illustrated, the guide wire passes through the treatment tool channel of the endoscope 5 and extends to the outside of a treatment tool insertion opening. This configuration allows an endoscope treatment tool of various kinds or the like to be inserted from the treatment tool insertion opening and allows the endoscope treatment tool to pass through until the bile duct.

Figure 6:
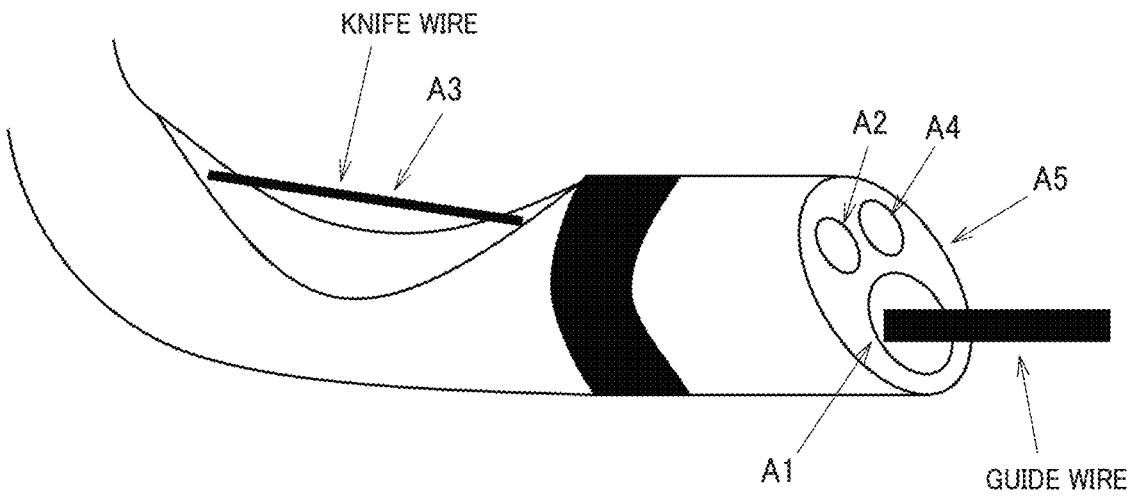
FIG. 6 is a view for conceptually describing a tip portion of an EST knife.

In a treatment by the EST, for example, an EST knife can be inserted into the bile duct along the placed and fixed guide wire. FIG. 6 is a view for conceptually describing a tip portion of the EST knife in accordance with the present embodiment. Note that in the present exemplary embodiment, a wide variety of known methods regarding the EST knife can be applied, and FIG. 6 merely illustrates an example. The EST knife has, for example, a configuration in which a plurality of lumens is arranged in an insulating tube. For example, a lumen indicated by A1 is arranged so that the above-mentioned guide wire passes therethrough. A knife wire passes through a lumen indicated by A2. In a case where tension is not applied to the knife wire, the knife wire is in a state of being stored in the insulating tube. A handle, which is not illustrated, is arranged on the treatment tool insertion opening side of the EST knife. When the handle is pulled toward the treatment tool insertion opening side, tension is applied to the knife wire, and the knife wire becomes in a state of being exposed from an opening portion of the insulating tube, as indicated by A3. For example, in a case where the papillary orifice is desired to be incised and expanded, a state indicated by A3 is created and high-frequency current is caused to flow through the knife wire, whereby tissues around the papillary orifice are burnt and incised. Note that a lumen indicated by A4 can be used for, for example, injection of the contrast agent. A surface in the tip portion indicated by A5 merely conceptually represents that the plurality of lumens is arranged in the EST knife and the knife wire does not project from the tip portion of the EST knife, and is not necessarily similar to the surface of the tip portion of the actual EST knife.

Examples of a treatment using the EST knife include removal of a gallstone. For example, although not illustrated, in a case where a gallstone in the bile duct is removed, performed is a treatment of inserting a basket treatment tool that passes through the guide wire into the bile duct and pulling out the basket treatment tool in a state where the gallstone is captured in a basket. In a case where a size of the gallstone is large, there is a method of crushing the gallstone. However, in terms of desirability of a method of incising and expanding the papillary orifice and then removing the gallstone to shorten treatment time, a treatment using the EST knife has been adopted in many cases. This is because the shorter treatment time can decrease the possibility of development of a complication or the like.

In incising the papillary orifice with the EST knife, it is extremely important to incise the papillary orifice in a direction along the bile duct. If the papillary orifice is incised in a direction other than the direction along the bile duct, there is a possibility of developing a complication such as damage on an artery and retroperitoneal perforation, which needs to be avoided. However, as is obvious from FIG. 5, since the bile duct is located on the deep side of the papillary orifice, a user cannot recognize a path of the bile duct directly from an endoscope image. More specifically, for example, in a case where a direction indicated by a dotted line region A10 in FIG. 7 is the direction along the bile duct, this region corresponds to a direction in which the papillary orifice should be incised in the EST, but it is difficult to recognize the region indicated by A10 using only the endoscope image as a clue. To address this, in the present embodiment, with the method that will be described below, the direction in which the papillary orifice should be incised with the EST knife is estimated and the guide display GM for guiding the estimated direction is displayed.

A processing example of the method in accordance with the present embodiment is described with reference to a flowchart in FIG. 8. First, processing of optimizing an intraluminal pressure is performed (step S100). For example, since a state where a lumen of the duodenum is contracted inhibits clear imaging of the duodenal papilla by the imager of the endoscope 5, an incision treatment by the EST, or the like, the intraluminal pressure is increased to extend the lumen of the duodenum. On the other hand, since the intestinal wall of the duodenum is thin, it is also necessary not to excessively extend the lumen of the duodenum. In step S100, for example, the user may manually operate an insufflation/deaeration device 7, which will be described later, while observing the endoscope image, or the processing system 3 may automatically operate the insufflation/deaeration device 7 as described later. Note that although the flow is not illustrated, the user periodically checks whether the intraluminal pressure is within a desired range from the endoscope image even after the intraluminal pressure is optimized in step S100.

Thereafter, the processor 10 performs processing of acquiring the endoscope image (step S200). For example, as described above, the processor 10 functions as the display control section 50, and acquires image data of the endoscope image captured by the imager at the tip of the endoscope 5. Thereafter, the processor 10 performs processing of estimating a summit line (step S300), which will be described later with reference to FIG. 9. Thereafter, the processor 10 performs display processing so as to superimpose the guide display GM based on the summit line estimated in step S300 on the endoscope image (step S400). The summit line mentioned herein is a linear region including a portion located on the closest side of the oral protrusion, and may have a certain width. Alternatively, the linear region corresponding to a ridge line of the oral protrusion may be considered as the summit line. The summit line has been empirically known as being corresponding to the path of the bile duct, but it is difficult to grasp the summit line directly from the endoscope image. Although the duodenal papilla includes the hooding fold and the circular fold as described above, it is considered that these structures differ substantially between individuals and have no correlation with the summit line.

FIG. 9 is a more detailed flowchart of the processing of estimating the summit line (step S300). The processor 10 performs processing of estimating a depth map of the oral protrusion and its surroundings from the endoscope image (step S302). The depth map represents information in which a depth of an object at each point of the map is allocated to the corresponding point. In the depth map in accordance with the present embodiment, for example, the depth of the object at each pixel in the endoscope image is allocated to the corresponding pixel.

Thereafter, the processor 10 performs processing of estimating the summit line of the oral protrusion from the depth map (step S304). Note that in the following description and illustration, estimation of the depth map of the oral protrusion and its surroundings from the endoscope image may be simply described as estimation of the depth map from the endoscope image. Note that in the following description and illustration, estimation of the summit line of the oral protrusion from the depth map may be simply described as estimation of the summit line from the depth map.

The processing described in the flowchart in FIG. 9 can be implemented by, for example, configuration of the processing section 100 as illustrated in FIG. 10. The processing section 100 in FIG. 10 includes the depth estimation section 110 and the summit line estimation section 120. That is, the processor 10 functions as the depth estimation section 110 in FIG. 10 to execute step S302 in FIG. 9, and functions as the summit line estimation section 120 in FIG. 10 to execute step S304 in FIG. 9.

More specifically, for example, the processing system 3 is configured like a configuration example illustrated in FIG. 11, whereby the processor 10 can be made to function as the depth estimation section 110. In FIG. 11, the processing system 3 further includes the memory 20, an input section 30, and an output section 40. The trained model 22 is stored in the memory 20.

The input section 30 is an interface that receives data from the outside. The output section 40 is an interface that transmits data inferred in an inference phase to the outside. The inference phase will be described later. Specific hardware of the input section 30 and the output section 40 is determined as appropriated in accordance with a function implemented by the processor 10. In a case where one processor 10 performs different types of inference, there is a case where data output from the output section 40 is re-input to the input section 30 by single inference, and the processor 10 performs another inference based on the re-input data. For example, assume a case where the depth estimation section 110 and the summit line estimation section 120, which will be described later with reference to FIG. 10, may be caused to function by the identical processor 10. In this case, the depth map output from the output section 40 as a result of the processor 10 functioning as the depth estimation section 110 is re-input to the input section 30, the processor 10 functions as the summit line estimation section 120, and summit line annotation data is output from the output section 40. Note that in the following description about processing using the trained model 22, the illustration and description of the input section 30 and the output section 40 will be omitted for convenience.

The trained model 22 is a program module that is generated by machine learning performed as supervised learning. The trained model 22 is generated by supervised learning based on a dataset that associates input data and a correct label with each other. More specifically, for example, the trained model 22 is generated by a training device, which is not illustrated, in a training phase. The training device stores an untrained model in which a weight coefficient is set as an initial value in a storage device, which is not illustrated. The weight coefficient will be described later. Training data as the dataset that associates the input data and the correct label with each other is input to the untrained model and feedback is made to the untrained model based on an inference result, whereby the weight coefficient is optimized and the trained model 22 is generated.

Note that FIG. 11 gives illustration so that one trained model 22 is stored in the memory 20, but the memory 20 may store a plurality of trained models 22. For example, in a case where the processor 10 functions as the depth estimation section 110 and also functions as a pressure determination section 60, which will be described later, the trained models 22 corresponding to respective functions are stored in the memory 20, and a trained model 22 corresponding to processing to be executed is selected as appropriate.

In the trained model 22 in accordance with the present embodiment, a neural network is included in at least part of the model. The neural network includes, although not illustrated, an input layer that takes input data, an intermediate layer that executes calculation based on an output from the input layer, and an output layer that outputs data based on an output from the intermediate layer. Note that the number of intermediate layers is not specifically limited. In addition, the number of nodes included in each of the intermediate layers is not specifically limited. In the intermediate layers, a node included in a given layer is connected to a node in an adjacent layer. A weight coefficient is assigned between connected nodes. Each node multiplies an output from a node in a former stage by the weight coefficient and obtains a total value of results of multiplication. Furthermore, each node adds a bias to the total value and applies an activation function to a result of addition to obtain an output from the node. This processing is sequentially executed from the input layer to the output layer, whereby an output from the neural network is obtained. As the activation function, various functions such as a sigmoid function and a rectified linear unit (ReLU) function are known, and a wide range of these functions can be applied in the present embodiment.

Alternatively, the trained model 22 may be generated by incremental learning performed on an existing trained model. For example, a method such as fine-tunning is used for the incremental learning. Specifically, for example, re-structuring such as addition of an output layer of the existing trained model is performed and machine learning using the above-mentioned training data is performed, whereby the weight coefficient is optimized.

The trained model 22 read out in a case where the processor 10 functions as the depth estimation section 110 is trained, for example, with a dataset of the endoscope image as the input data and the depth map as the correct label. In the inference phase, the endoscope image is then input to the input section 30, and the processor 10 reads out the corresponding trained model 22 from the memory 20 and inputs the endoscope image to the trained model 22. With this configuration, the inferred depth map is output from the trained model 22 via the output section 40.

Note that a monocular depth estimation model that is publicly available as an open source may serve as the trained model 22 for causing the processor 10 to function as the depth estimation section 110. Since this configuration eliminates the need for arranging the above-mentioned training phase, it is possible to reduce a burden to prepare training data. The burden to prepare training data mentioned herein is, for example, a burden to prepare the endoscope 5 on which a depth sensor or the like is mounted to create the depth map of the duodenal papilla as the correct label. Note that modification such as execution of the above-mentioned incremental learning may be made to the above-mentioned monocular depth estimation mode.

In this manner, the processor 10 functions as the depth estimation section 110 to perform step S302 in FIG. 9. For example, when an endoscope image in a region indicated by A21 in FIG. 12 is input, a depth map indicated by A22 is output. A depth value at each pixel constituting the depth map indicated by A22 is included. Note that the depth map in accordance with the present embodiment is displayed in four to five shades of gray, but may be displayed in more shades of gray. In addition, the depth map indicated by A22 is expressed by excluding irregularities due to the hooding fold, the circular fold, and the frenum, and the like, for easier understanding of the gist of the present disclosure. The same applies to the depth map that will be described later. While A21 represents the endoscope image of the duodenal papilla into which the treatment tool is not inserted for explanatory convenience, the endoscope image of the papillary portion may be, for example, the one in a phase in which the above-mentioned guide wire is placed and fixed in the bile duct or the one in a phase in which an EST treatment tool is further inserted, and is determined as appropriate.

The processor 10 performs step S304 in FIG. 9 by reading out the corresponding trained model 22, and functions as the summit line estimation section 120. The trained model 22 in this case has been machine-learned with a dataset of the depth map output from the depth estimation section 110 as the input data and the summit line annotation data as the correct label. Note that an endoscope image corresponding to the depth map may be further added as input data to increase accuracy in the inference phase.

Note that step S304 in FIG. 9 can be implemented by a method not using machine learning. For example, the processor 10 calculates an average value of depth values for each predetermined number of pixels with the depth map output from the depth estimation section 110 as the input data, and estimates the summit line based on the calculated value.

In this manner, the processor 10 functions as the summit line estimation section 120, and thereby estimates, for example, a region indicated by A24 as the summit line based on a region indicated by A23 in FIG. 12. The region indicated by A23 is a region in shades of gray indicating the closer side in the depth map. The processor 10 then generates image data of the guide display GM based on the estimated summit line, and outputs the generated image data of the guide display GM.

Such processing of estimating the summit line (step S300) is performed, whereby an endoscope image as indicated by A31 in FIG. 13 is displayed on the display device 9, which will be described later, as a result of step S400. The endoscope image indicated by A31 is displayed so that the guide display GM is superimposed on the duodenal papilla.

As described above, the processing system 3 in accordance with the present embodiment includes the processor 10 including hardware. The processor 10 acquires the endoscope image in which the duodenal papilla including the oral protrusion is imaged, estimates the depth map of the region including the duodenal papilla from the endoscope image, estimates the summit line of the oral protrusion from the estimated depth map, and performs display processing so as to superimpose the guide display GM based on the estimated summit line on the endoscope image. It is impossible to grasp the path of the bile duct directly from the endoscope image in which the duodenal papilla is seen. The path of the bile duct is known to have a correlation with the shape of the oral protrusion, but since the endoscope image is a two-dimensional image without information regarding a depth direction, it is difficult to grasp the shape of the oral protrusion directly from the endoscope image in which the duodenal papilla is imaged. In this regard, the processing system 3 in accordance with the present embodiment estimates the depth map from the endoscope image, and can thereby estimate the shape of the oral protrusion based on the depth map. In addition, since the processing system 3 estimates the summit line of the oral protrusion from the depth map and performs display so as to superimpose the guide display GM based on the estimated summit line on the endoscope image, the user can grasp the summit line of the oral protrusion by seeing the guide display GM. This can enhance convenience in the treatment on the bile duct.

Although, for example, a method of mounting a three-dimensional imaging device on the endoscope tip portion has also been proposed, there is a difficult issue to actually mount such an imaging device on the endoscope tip portion due to increase of a size of the endoscope tip portion or other factors. In this regard, by applying the method in accordance with the present embodiment, the depth map is estimated from a normal endoscope image and the summit line of the oral protrusion is estimated, whereby the path of the bile duct in the duodenal papilla can be estimated without mounting of the three-dimensional imaging device.

The method in accordance with the present embodiment may be implemented as the endoscope system 1. That is, the endoscope system 1 in accordance with the present embodiment includes the processing system 3 and the endoscope 5 which have been described above. As a result, an effect that is similar to the above-mentioned effect can be obtained.

In addition, the method in accordance with the present embodiment may be implemented as a processing method. That is, in the processing method in accordance with the present embodiment, the processing of acquiring the endoscope image in which the duodenal papilla including the oral protrusion is imaged is performed (step S200), the processing of estimating the depth map of the region including the duodenal papilla from the endoscope image is performed (step S302), and the processing of estimating the summit line of the oral protrusion from the estimated depth map is performed (step S304). Additionally, in the processing method in accordance with the present embodiment, the display processing so as to superimpose the guide display based on the estimated summit line on the endoscope image is further performed (step S400). As a result, an effect that is similar to the above-mentioned effect can be obtained.

Furthermore, in the processing system 3 in accordance with the present embodiment, the guide display GM may be an incision guide display in the EST. The same applies to a case where the method in accordance with the present embodiment is implemented as the processing method. That is, in the processing method in accordance with the present embodiment, the guide display GM may be the incision guide display in the EST. With this configuration, the user can perform the EST while estimating the summit line of the oral protrusion. Specifically, for example, the user moves the knife wire of the EST knife along the guide display GM while energizing the knife wire, and can thereby perform incision in a desired direction as indicated by A32 in FIG. 13.

Additionally, the processing system 3 in accordance with the present embodiment may include the memory 20 that stores the trained model 22 that has been trained to estimate the depth map from the input image. Furthermore, the processor 10 may input the endoscope image to the trained model 22 to estimate the depth map. With this configuration, it is possible to construct the processing system 3 that estimates the depth map using the trained model 22 that has been machine-learned.

The method in accordance with the present embodiment is not limited to the above-mentioned method, and can be modified in various manners such as addition of another feature. For example, the processing system 3 in accordance with the present embodiment may automatically perform step S100 in FIG. 8. Specifically, for example, the processing system 3 has a configuration like a configuration example illustrated in FIG. 14, and a processing example indicated in a flowchart in FIG. 15 is incorporated in step S100 in FIG. 8, whereby automation of processing corresponding to step S100 can be implemented. Alternatively, after performing step S200 and subsequent steps in FIG. 8, the processing system 3 may perform timer interruption processing or the like to periodically perform processing in FIG. 15. With this configuration, it is possible to maintain an intraluminal pressure appropriate for execution of the method in accordance with the present embodiment.

FIG. 14 is a block diagram illustrating the endoscope system 1 in accordance with the present embodiment in a more detailed manner. The endoscope system 1 further includes, in addition to the processing system 3 and the endoscope 5 that have been described above, the insufflation/deaeration device 7 and the display device 9. The processor 10 included in the processing system 3 further includes, in addition to the display control section 50 and the processing section 100 that have been described above, the pressure determination section 60.

The pressure determination section 60 makes determination about the intraluminal pressure of the duodenum based on the endoscope image received from the endoscope 5 via the display control section 50, and controls the insufflation/deaeration device 7 based on a result of the determination. The insufflation/deaeration device 7 is connected to the endoscope tip portion via an internal channel of the insertion portion. The internal channel is not illustrated. With this configuration, it is possible to perform insufflation or deaeration on the lumen of the duodenum via the endoscope tip portion. Note that the insufflation/deaeration device 7 is a known device, and a detailed description thereof is omitted.

The processing example of the flowchart in FIG. 15 is now described. The processor 10 estimates the intraluminal pressure of the duodenum from the endoscope image (step S102), and performs processing of determining whether or not the estimated intraluminal pressure of the duodenum is higher than a predetermined range (step S110). A means for implementing step S102 will be described later. The predetermined range is determined by the user as appropriate based on cases in the past or the like. In a case where the estimated intraluminal pressure of the duodenum is higher than the predetermined range (YES in step S110), the processor 10 performs processing of deaerating the inside of the lumen of the duodenum (step S112), and then ends the flow. This can further decrease the intraluminal pressure of the duodenum. On the other hand, in a case of determining that the estimated intraluminal pressure of the duodenum is not higher than the predetermined range (NO in step S110), the processor 10 performs processing of determining whether or not the estimated intraluminal pressure is lower than the predetermined range (step S120). In a case of determining that the estimated pressure is lower than the predetermined range (YES in step S120), the processor 10 performs processing of insufflating the inside of the lumen of the duodenum (step S122), and ends the flow. This can further increase the intraluminal pressure of the duodenum.

On the other hand, in a case of determining that the estimated pressure is not lower than the predetermined range (NO in step S120), the processor 10 ends the flow. In other words, in a case of NO in step S110 and NO in step S120, it is determined that the estimated pressure is within the predetermined range and there is no need for performing insufflation or deaeration.

The trained model 22 read out in a case where the processor 10 functions as the pressure determination section 60 has been machine-learned with, for example, the endoscope image in which the inside of the lumen of the duodenum is imaged and a dataset in which a feature amount such as the number of wrinkles inside the lumen of the duodenum and a depth of a wrinkle and a result of determination about the intraluminal pressure of the duodenum are associated with the endoscope image. The result of determination about the intraluminal pressure of the duodenum mentioned herein is a result of determination by which classification has been made into "the intraluminal pressure of the duodenum is a pressure within the predetermined range", "the intraluminal pressure of the duodenum is higher than the predetermined range", "the intraluminal pressure of the duodenum is lower than the predetermined range", and the like, and functions as the correct label.

In the inference phase, the endoscope image in which the inside of the lumen of the duodenum is imaged is input as the input data to the input section 30. The processor 10 then reads out the trained model 22 from the memory 20. With this configuration, the processor 10 functions as the pressure determination section 60, and performs processing of extracting the feature amount such as the number of wrinkles and the depth of the wrinkle from the input endoscope image, processing of selecting a correct label corresponding to the extracted feature amount, and processing of outputting the selected correct label as output data via the output section 40. With this processing, step S102 in FIG. 15 can be implemented. The processing in step S102 and subsequent steps is then performed in accordance with contents of the selected correct label.

In this manner, in the processing system 3 in accordance with the present embodiment, the processor 10 estimates whether or not the intraluminal pressure of the duodenum is within a range of an appropriate pressure based on the endoscope image (step S102). In a case where the intraluminal pressure of the duodenum is outside the range of the appropriate pressure, the processor 10 performs insufflation or deaeration processing so that the intraluminal pressure of the duodenum is within the range of the appropriate pressure (steps S112 and S122). The same applies to a case where the method in accordance with the present embodiment is implemented as the processing method. That is, the processing method in accordance with the present embodiment further includes performing processing of estimating whether or not the intraluminal pressure of the duodenum is within the range of the appropriate pressure based on the endoscope image, and performing, in a case where the intraluminal pressure of the duodenum is outside the range of the appropriate pressure, insufflation or deaeration processing so that the intraluminal pressure of the duodenum becomes within the range of the appropriate pressure. As a result, it is possible to put the inside of the lumen of the duodenum in an appropriate state for estimation of the summit line, incision in the EST, or the like.

Note that among the above-mentioned correct labels, for example, the label of "the intraluminal pressure of the duodenum is higher than the predetermined range" may be further graded as a plurality of ranks. In addition, the processor 10 may select a command to be output from the pressure determination section 60 to the insufflation/deaeration device 7 so as to correspond to the output rank, and output the selected command to the insufflation/deaeration device 7. The same applies to the label of "the intraluminal pressure of the duodenum is lower than the predetermined range". As a result, it is possible to control the insufflation/deaeration device 7 more accurately.

Although not illustrated, the processing section 100 in each of FIGS. 20, 22, 26, 29, 32, 37, and 44 may be configured to control the pressure determination section 60.

Alternatively, for example, the present embodiment may be implemented as a method of acquiring a plurality of endoscope images that can have different shapes of the duodenal papilla, and estimating the summit line based on depth maps estimated from the respective endoscope images. For example, the processing section 100 is configured as a configuration example illustrated in FIG. 16, step S200 in FIG. 8 is implemented as a processing example described in a flowchart in FIG. 17, and step S300 in FIG. 8 is implemented as a processing example described in a flowchart in FIG. 18, whereby the above-mentioned method can be implemented. The processing section 100 illustrated in FIG. 16 is different from the processing section 100 illustrated in FIG. 10 in that the summit line estimation section 120 further includes a depth estimation result subtraction section 122.

The processing of acquiring the endoscope image (step S200) described in FIG. 17 is now described. The processor 10 acquires a first endoscope image (step S202), and thereafter acquires a second endoscope image (step S204). Thereafter, the processing returns to the flowchart in FIG. 8, and the processor 10 performs the processing of estimating the summit line (step S300) and the processing in step S400.

A combination of the first endoscope image and the second endoscope image is only required to be a combination of endoscope images that are different in shape of the duodenal papilla and is not specifically limited. For example, the first endoscope image includes, as indicated by A41 in FIG. 19, the oral protrusion, and the endoscope image of the duodenal papilla in the state where the treatment tool is not inserted can be adopted as the first endoscope image. Additionally, the second endoscope image includes, for example, as indicated by A42 in FIG. 19, the oral protrusion, and the endoscope image of the duodenal papilla in the state where the treatment tool is inserted can be adopted as the second endoscope image. The state where the second endoscope image indicated by A42 is captured may be, for example, a state where the guide wire as the treatment tool is inserted, but may be a state where the above-mentioned cannula is inserted or a state where the EST knife is inserted and immediately before the EST is started. In this manner, in the processing system 3 in accordance with the present embodiment, the processor 10 estimates the summit line based on the first endoscope image in the state where the treatment tool is not inserted and the second endoscope image in the state where the treatment tool is inserted. The same applies to a case where the method in accordance with the present embodiment is implemented as the processing method. That is, in the processing method in accordance with the present embodiment, performed is the processing of estimating the summit line based on the first endoscope image in the state where the treatment tool is not inserted and the second endoscope image in the state where the treatment tool is inserted (steps S202, S204, and S300). As a result, it is possible to estimate the path of the bile duct more accurately. Since the treatment tool is inserted into the bile duct, it is considered that a change in the summit line corresponds to a change in the path of the bile duct.

Note that step S202 is not limited to the processing of acquiring the first endoscope image captured by the imager of the endoscope 5 in real time, but may be, for example, processing of selecting the first endoscope image preliminarily stored in the memory 20 or the like. The same applies to step S204. For example, in a case where the endoscope image of the duodenal papilla in the state where the treatment tool is not inserted serves as the first endoscope image as described above, for example, an endoscope image captured when the endoscope tip portion is aligned with the duodenal papilla at the time of execution of the ERCP is only required to be separately stored in the memory 20 or the like. Additionally, in a case where an endoscope image of the duodenal papilla captured at a timing at which the guide wire is inserted into the bile duct for the first time serves as the second endoscope image, the endoscope image captured at the timing is only required to be separately stored in the memory 20 or the like. Alternatively, in a case where an endoscope image of the duodenal papilla captured at a timing immediately before the start of the EST serves as the second endoscope image, processing of acquiring an endoscope image captured with the imager of the endoscope 5 in real time is only required to be performed in step S204.

The processing of estimating the summit line (step S300) described in FIG. 18 is now described. The processor 10 estimates the first depth map from the first endoscope image (step S310), estimates the second depth map from the second endoscope image (step S320), and estimates the summit line based on a difference between the first depth map and the second depth map (step S350). Steps S310 and S320 in FIG. 18 are processing corresponding to step S302 in FIG. 9, and for example, the first depth map indicated by A61 is generated based on the first endoscope image indicated by A41 in FIG. 19 as a result of step S310. Similarly, the second depth map indicated by A62 is generated based on the second endoscope image indicated by A42 in FIG. 19 as a result of step S320. Note that the first depth map indicated by A61 in FIG. 19 displays a portion corresponding to an endoscope image inside a dotted line frame among the first endoscope image indicated by A41 for explanatory convenience. Similarly, the second depth map indicated by A62 displays a portion corresponding to an endoscope image inside a dotted line frame among the second endoscope image indicated by A42.

Thereafter, the processor 10 functions as the depth estimation result subtraction section 122, and obtains a difference between the second depth map indicated by A62 and the first depth map indicated by A61. That is, the processor 10 obtains a difference in gradation values of each pixel between the first and second depth maps, and an aggregation of pixels whose difference values are relatively high is estimated to be a region that has been changed in depth with the insertion of the treatment tool. In a case where the treatment tool is the guide wire, since the guide wire passes through the bile duct as described above with reference to FIG. 5, the above-mentioned region that has been changed in depth can be estimated to be a region through which the bile duct passes.

In this manner, in the processing system 3 in accordance with the present embodiment, the processor 10 estimates the summit line based on the difference between the first depth map estimated from the first endoscope image and the second depth map estimated from the second endoscope image. With this configuration, it is possible to construct the processing system 3 that estimates the summit line based on the difference between the depth maps in different states. The same applies to a case where the method in accordance with the present embodiment is implemented as the processing method. That is, in the processing method in accordance with the present embodiment, performed is the processing of estimating the summit line based on the difference between the first depth map estimated from the first endoscope image and the second depth map estimated from the second endoscope image (steps S310, S320, and S350). With this configuration, it is possible to construct the processing method to estimate the summit line based on the difference between the depth maps in different states.

As described above with reference to FIG. 11 and the like, since step S302 in FIG. 9 is performed with use of the trained model 22 that has been machine-learned, steps S310 and S320 in FIG. 18 are similarly performed with use of the trained model 22. That is, the processing system 3 in accordance with the present embodiment includes the memory 20 that stores the trained model 22 that has been trained to estimate the depth map from the input image. The processor 10 inputs the first endoscope image to the trained model 22 to estimate the first depth map, inputs the second endoscope image to the trained model 22 to estimate the second depth map, and estimates the summit line based on the first depth map and the second depth map. With this configuration, it is possible to construct the processing system 3 that estimates the summit line based on the two depth maps using the trained model 22 that has been machine-learned.

Alternatively, for example, the present embodiment may be implemented as a method of performing alignment and thereafter estimating the summit line. For example, the processing section 100 is configured as a configuration example illustrated in FIG. 20, step S200 in FIG. 8 is implemented as a processing example described in the flowchart in FIG. 17, and step S300 in FIG. 8 is implemented as a processing example described in a flowchart in FIG. 21, whereby the above-mentioned method can be implemented. The configuration example of the processing section 100 in FIG. 20 is different from the configuration example of the processing section 100 in FIG. 16 in further including a key point detection section 130 and a first depth estimation result alignment section 141. Note that a description about processing that has been already described is omitted.

The processing of estimating the summit line (step S300) in FIG. 21 is now described. The processor 10 performs the processing of estimating the first depth map from the first endoscope image (step S310) similarly to FIG. 18, and also functions as the key point detection section 130 to detect a key point from the first endoscope image (step S312). The key point mentioned herein is position information that serves as a criterion for alignment between the first depth map and the second depth map, and is, specifically, the papillary orifice, the hooding fold, the frenum, or the like. The key point can also be called a feature point or a land mark. Processing of causing the processor 10 to function as the key point detection section 130 corresponds to step S312.

Step S312 is performed with use of the trained model 22 that has been machine-learned. For example, the trained model 22 that is read out in a case where the processor 10 functions as the key point detection section 130 has been machine-learned so as to output, for example, when the endoscope image in which the duodenal papilla is imaged is input thereto, an endoscope image in which the papillary orifice or the like serving as the key point is segmented. A convolutional neural network (CNN) used in the field of image recognition, a recurrent neural network (RNN), or a model that has been further developed from the CNN or the RNN may be used for at least part of the trained model 22 regarding step S312. Examples of the model that has been further developed from the CNN or the like include a Segmentation Network (SegNet), a Fully Convolutional Network (FCN), and a U-Shaped Network (U-Net), a Pyramid Scene Parsing Network (PSPNet), You Only Look Once (YOLO), and Single Shot Multi-Box Detector (SSD).

Thereafter, the processor 10 performs the processing of estimating the second depth map from the second endoscope image similarly to FIG. 18 (step S320), and also performs processing of detecting the key point from the second endoscope image (step S322). Step S322 is performed with use of the trained model 22 that has been machine-learned, similarly to the above-mentioned step S312.

Thereafter, the processor 10 functions as the first depth estimation result alignment section 141 to perform processing of aligning the first depth map and the second depth map using the detected key point as the criterion (step S330). For example, as indicated by A51 in FIG. 19 which has been described above, the papillary orifice is detected as the key point from the first endoscope image as a result of step S312. Similarly, for example, as indicated by A52 in FIG. 19, the papillary orifice is detected as the key point from the second endoscope image as a result of step S322.

The processor 10 then functions as the first depth estimation result alignment section 141, and identifies, for example, a position indicated by A71 in FIG. 19 as the position of the papillary orifice in the first depth map based on coordinate information of the detected key point in A51. Note that in a case where the key point indicated by A51 is detected as a region, a center-of-gravity position in the indicated region is only required to be identified as the position indicated by A71. Similarly, the processor 10 identifies, for example, the position indicated by A72 in FIG. 19 as the position of the papillary orifice in the second depth map based on the coordinate information of the detected key point in A52. The processor 10 then converts positional coordinates of either the first depth map or the second depth map so that positional coordinates indicated by A71 and positional coordinates indicated by A72 become identical coordinates. Thereafter, the processor 10 performs the above-mentioned step S350 to estimate the summit line.

Note that step S330 can also be performed with use of the trained model 22. For example, the trained model 22 is only required to be trained with a dataset that associates, for example, an endoscope image, a key point in the endoscope image, and information regarding a correspondence relationship of key points between different endoscope images.

For example, the processing section 100 is configured as a configuration example illustrated in FIG. 22, step S200 in FIG. 8 is implemented as a processing example indicated in the flowchart in FIG. 17, which has been described above, and step S300 in FIG. 8 is implemented as a processing example described in a flowchart in FIG. 23, whereby the above-mentioned method can be implemented similarly. The configuration example of the processing section 100 in FIG. 22 is different from the configuration example of the processing section 100 in FIG. 16 in further including a point group data generation section 132 and a second depth estimation result alignment section 142.

The processing of estimating the summit line (step S300) in FIG. 23 is now described. The processor 10 performs the processing of estimating the first depth map from the first endoscope image (step S310) similarly to FIG. 18, and thereafter performs processing of generating first point group data from the first depth map (step S314). For example, the processor 10 functions as the point group data generation section 132 to acquire a depth map as indicated by A63 in FIG. 24 as the first depth map from the depth estimation section 110 and generate point group data as indicated by A83 based on a predetermined algorithm. The predetermined algorithm is only required to be a known method to generate point group data from a depth map.

Thereafter, the processor 10 performs the processing of estimating the second depth map from the second endoscope image (step S320) similarly to FIG. 18, and thereafter performs processing of generating second point group data from the second depth map (step S324). The processing in step S324 is similar to the above-described processing in step S314.

The first endoscope image and the second endoscope image in the processing example in FIG. 23 are similar to those in the processing example in FIG. 21. That is, the first endoscope image in the processing example in FIG. 23 is, for example, the endoscope image of the duodenal papilla in the state where the treatment tool is not inserted as illustrated in A44 in FIG. 25, and the second endoscope image in the processing example in FIG. 23 is, for example, the endoscope image of the duodenal papilla in the state where the treatment tool is inserted as illustrated in A45 in FIG. 25. With this configuration, from the first endoscope image indicated by A44, the first depth map, which is not illustrated in FIG. 25, is generated as a result of step S310, and the first point group data indicated by A84 is generated based on the first depth map as a result of step S314. Similarly, from the second endoscope image indicated by A45, the second depth map, which is not illustrated in FIG. 25, is generated as a result of step S320, and the second point group data indicated by A85 is generated based on the second depth map as a result of step S324.

Thereafter, the processor 10 functions as the second depth estimation result alignment section 142 to perform processing of aligning the first depth map and the second depth map based on the first point group data and the second point group data (step S340). The processing in step S340 can be implemented by, for example, a method using an iterative closest point (ICP) algorithm or the like. Although a detailed description of the ICP algorithm is omitted because it is a known method, a position and orientation between a coordinate system of the first point group data and a coordinate system of the second point group data are adjusted so that, with respect to each point of one of these pieces of point group data, a point the most closest to this point is searched from the other point group data and these points are associated with each other to minimize a difference in points that have been associated with each other. With this configuration, for example, a difference between each point constituting a contour portion indicated by A94 and each point constituting a contour portion indicated by A95 is minimized, and matching between the first point group data and the second point group data is performed. The processor 10 then adjusts a positional relationship between the first depth map and the second depth map so as to correspond to the adjustment of the coordinate systems of the pieces of point group data.

Note that step S340 can be performed with use of the trained model 22. For example, the trained model 22 is only required to be trained with a dataset using a combination of pieces of point group data whose corresponding positional coordinates are different as the input data and coordinate converted data used when a positional relationship is adjusted as the correct label. Thereafter, the processor 10 estimates the summit line based on the difference between the first depth map and the second depth map whose positional relationship has been adjusted (step S350).

Consequently, in the processing system 3 in accordance with the present embodiment, the processor 10 estimates the summit line based on the difference between the first depth map and the second depth map in the state where the position of the duodenal papilla seen in the first endoscope image and the position of the duodenal papilla seen in the second endoscope image are aligned with each other. The same applies to a case where the method in accordance with the present embodiment is implemented as the processing method. That is, in the processing method in accordance with the present embodiment, performed is the processing of estimating the summit line based on the difference between the first depth map and the second depth map in the state where the position of the duodenal papilla seen in the first endoscope image and the position of the duodenal papilla seen in the second endoscope image are aligned with each other (steps S330, S340, and S350). As a result, it is possible to further increase the accuracy of estimation of the summit line. There is a possibility that the endoscope tip portion moves in a process of inserting the treatment tool, and the position of the duodenal papilla in the first endoscope image and the position of the duodenal papilla in the second endoscope image are not matched with each other. In this regard, by applying the method in accordance with the present embodiment, it is possible to match the positions of the duodenal papilla before and after the insertion of the treatment tool, whereby it becomes possible to obtain the difference between the first depth map and the second depth map more accurately.

Alternatively, for example, the present embodiment may be implemented as a method of setting a position of one end of the guide display GM. For example, the processing section 100 is only required to be configured as a configuration example illustrated in FIG. 26, and step S300 in FIG. 8 is only required to be implemented as a processing example described in a flowchart in FIG. 27. The configuration example of the processing section 100 in FIG. 26 is different from the configuration example of the processing section 100 in FIG. 16 in further including a papillary orifice detection section 150.

The processing of estimating the summit line (step S300) in FIG. 27 is now described. The processor 10 the performs processing of estimating the depth map from the endoscope image (step S302) similarly to the above-description, and also functions as the papillary orifice detection section 150 to perform processing of detecting the papillary orifice on the endoscope image (step S360).

Step S360 is performed with use of the trained model 22 that has been machine-learned. That is, the trained model 22 read out in a case where the processor 10 functions as the papillary orifice detection section 150 is machine-learned so as to output, for example, when the endoscope image in which the duodenal papilla is imaged is input thereto, the endoscope image in which the papillary orifice is segmented or the like.

The processor 10 then performs processing of estimating the summit line using the detected papillary orifice as the criterion (step S362). For example, in FIG. 28, assume that a region indicated by B1 is a region of the papillary orifice region detected in step S360, and a region indicated by B2 is a region that is estimated to be the closest side in the depth map generated in step S302. In this case, for example, the processor 10 calculates barycentric coordinates of the region B1, and sets a barycentric coordinate point as indicated by B3. Thereafter, the processor 10 performs processing of setting a virtual line passing through the barycentric coordinates B3 and a central portion of the region B2 as the summit line as indicated by B4. Assume that a direction of the line indicated by B4 is matched with a vertical direction of the plane of paper for explanatory convenience. The same applies to FIG. 34, which will be described later. Although not illustrated, the processor 10 then estimates, among the line indicated by B4, a line that starts from the point indicated by B3 and that includes the region B2 as the summit line, and displays the guide display GM corresponding to the estimated summit line.

In this manner, in the processing system 3 in accordance with the present embodiment, the processor 10 detects the papillary orifice based on the endoscope image, and estimates the summit line that starts from the papillary orifice. The same applies to the case where the method in accordance with the present embodiment is implemented as the processing method. That is, in the processing method in accordance with the present embodiment, the processing of detecting the papillary orifice based on the endoscope image is further performed (step S360), and the processing of estimating the summit line that starts from the papillary orifice is performed (step S362). With this configuration, it is possible to display the guide display GM that starts from the papillary orifice. The summit line does not necessarily include the papillary orifice. However, since the EST is a manipulation of incising and extending the papillary orifice, display of the guide display GM that starts from the papillary orifice is convenient for the user.

Additionally, for example, the processing section 100 is configured as a configuration example illustrated in FIG. 29, and step S300 in FIG. 8 is implemented as a processing example described in a flowchart in FIG. 30, whereby a similar method can be implemented. The configuration example of the processing section 100 in FIG. 29 is different from the configuration example of the processing section 100 in FIG. 16 in further including a treatment tool detection section 152.

The processing of estimating the summit line (step S300) in FIG. 30 is now described. The processor 10 functions as the depth estimation section 110 to perform the above-mentioned step S302, and also functions as the treatment tool detection section 152 to perform processing of detecting the treatment tool on the endoscope image (step S370).

Step S370 is performed with use of the trained model 22 that has been machine-learned similarly to step S360. That is, the trained model 22 read out in a case where the processor 10 functions as the treatment tool detection section 152 is machine-learned so as to output, for example, when the endoscope image in which the duodenal papilla into which the treatment tool is inserted is imaged is input thereto, the endoscope image in which the imaged treatment tool region is segmented or the like.

The processor 10 then performs processing of estimating the summit line using the detected treatment tool as a criterion (step S372). For example, in FIG. 31, assume that a region indicated by B11 is a tip region of a portion of the treatment tool that is detected as a result of step S370 and seen in the endoscope image, and a region indicated by B12 is a region that is estimated to be a region on the closest side in the depth map generated in step S302. In this case, the processor 10 performs processing of setting, as indicated by B13, a virtual line passing through a central portion of the region indicated by B11 and a central portion of the region indicated by B12. Although not illustrated, the processor 10 then estimates, among the line indicated by B13, a line that starts from the region indicated by B11 and that includes the region B12 as the summit line, and displays the guide display GM corresponding to the estimated summit line.

In this manner, in the processing system 3 in accordance with the present embodiment, the processor 10 detects the portion of the treatment tool seen in the endoscope image based on the endoscope image, and estimates the summit line that starts from the tip of the detected portion. The same applies to the case where the method in accordance with the present embodiment is implemented as the processing method. That is, in the processing method in accordance with the present embodiment, the processing of detecting the portion of the treatment tool seen in the endoscope image based on the endoscope image is further performed (step S370), and the processing of estimating the summit line that starts from the tip of the detected portion is performed (step S372). With this configuration, it is possible to display the guide display GM that starts from one end of the treatment tool. To perform the EST, display of the guide display GM that starts from the EST knife as the treatment tool is convenient for the user. Although there is a case where the papillary orifice itself cannot be visually recognized in a clear manner from the endoscope image depending on a treatment tool, since the position of the tip of the portion of the treatment tool seen in the endoscope image corresponds to the position of the papillary orifice, the method described with reference to FIGS. 29 to 31 can be expected to provide a similar effect to that of the method described with reference to FIGS. 26 to 28.

Alternatively, the present embodiment may be implemented as, for example, a method of displaying the guide display GM to have a certain range. Specifically, for example, the processing section 100 is configured as a configuration example illustrated in FIG. 32, and step S300 in FIG. 8 is implemented as a processing example described in a flowchart in FIG. 33, whereby the above-mentioned method can be implemented. The configuration example of the processing section 100 in FIG. 32 is different from the configuration example of the processing section 100 in FIG. 26 in further including the incision region generation section 160. Although not illustrated, the processing section 100 in FIG. 32 may have a configuration in which the processing section 100 in FIG. 29 further includes the incision region generation section 160. In this case, processing corresponding to step S364, which will be described later, is only required to be added to the flowchart in FIG. 30.

The processing of estimating the summit line (step S300) in FIG. 33 is now described. Note that a description about processing that is similar to that in FIG. 27 is omitted. The processor 10 performs steps S302, S360, and S362 in FIG. 27, thereafter functions as the incision region generation section 160, and performs processing of generating a region indicating between an eleven o'clock direction and a twelve o'clock direction when the estimated summit line is assumed to be the twelve o'clock direction as an incision region (step S364). Note that the twelve o'clock direction mentioned herein is a twelve o'clock direction centered on one end of the estimated summit line on the papillary orifice side.

For example, the summit line is estimated in step S302. As a result of execution of steps S360 and S362, as illustrated in FIG. 34, the guide display GM that starts from the center-of-gravity position of the papillary orifice is displayed in a direction that is matched with the vertical direction of the plane of paper. The processor 10 then functions as the incision region generation section 160, and performs processing of generating a virtual line indicated by B21, and processing of generating a region indicated by B22 as the incision region.

Note that the processing in FIG. 33 or the like can also be applied to a case where a structure of organs is changed by a predetermined surgical treatment. In other words, although how an endoscope image looks becomes different when the structure of the organs is changed, the processing in FIG. 33 or the like can be applied regardless of how the endoscope image looks.

A specific description will be given with reference to FIGS. 35 and 36. In a case where the structure of the organs is changed by, for example, Billroth's operation II as illustrated in FIG. 35, as the predetermined surgical treatment, this case is different from the case illustrated in FIG. 2 in that the endoscope tip portion is inserted from the jejunum side toward the duodenal papilla when the EST or the like is performed. Note that in the Billroth's operation II, as illustrated in C1 in FIG. 35, after the pylorus side of the stomach is resected for the purpose of an obesity treatment, resection of stomach cancer, or the like, a stump of the remnant stomach and the jejunum are anastomosed, whereby a bypass for a passage of food is created. In addition, as illustrated in C2, an end portion of the duodenum is suture-closed. Note that obesity mentioned is a state where excessive body fat is accumulated in such a degree as to cause reduction of life expectancy, a health problem, and the like. Obesity surgery is performed in a case where a BMI exceeds a certain value, or the BMI exceeds the certain value and there is a comorbidity. The BMI is an abbreviation for body mass index. Note that examples of the predetermined surgical treatment also include a Roux-en-Y gastric bypass operation.

For example, assume that the duodenal papilla exits on a side wall of a lumen indicated by C11 in FIG. 36, the duodenal papilla has a structure indicated by C12, and the papillary orifice is located at a position indicated by C22. In FIG. 36, assume that a direction DR1 is a direction along a direction from the stomach side toward the duodenum side, and a direction DR2 is the opposite direction of the direction DR1, that is, a direction along a direction from the jejunum side toward the duodenum side. Assume that a direction DR3 and a direction DR4 are directions orthogonal to the direction DR1 and directions along the wall surface of the lumen, and the direction DR3 faces upward with respect to the plane of paper.

In a case where the structure of the organs is not changed as illustrated in FIG. 2, the endoscope tip portion is inserted toward the direction DR1. Since the direction DR1 faces upward, the endoscope image captured by the imager in the endoscope tip portion is an image indicated by C13. In contrast, in a case where the structure of the organs is changed as illustrated in FIG. 35, the endoscope tip portion is inserted toward the direction DR2. Since the direction DR2 faces upward, the endoscope image captured by the imager in the endoscope tip portion inserted toward the direction DR2 is an image as indicated by C14. That is, the endoscope image indicated by C13 and the endoscope image indicated by C14 have a relationship of being rotated by 180 degrees with the respect to the direction orthogonal to the endoscope image as an axis.

In the case where the structure of the organs is not changed as illustrated in FIG. 2, the eleven o'clock direction, when a direction that is centered on one end of the guide display GM and that the guide display GM faces is the twelve o'clock, is a direction indicated by dotted line C23, and a region between the guide display GM and the dotted line C23 is the incision region. In contrast, in the case where the structure of the organs is changed as illustrated in FIG. 35, the eleven o'clock direction, when the direction that is centered on one end of the guide display GM and that the guide display GM faces is the twelve o'clock, is a direction indicated by dotted line C24, and a region between the guide display GM and the dotted line C24 is the incision region.

In this manner, when looking at only the endoscope image indicated by C14, it seems that the direction of the guide display GM and the direction of the dotted line C24 do not have a relationship between twelve o'clock and eleven o'clock, but, in the present embodiment, one end of the summit line on the papillary orifice side is defined as the center for twelve o'clock so that the incision region can be displayed accurately. As described above, in the processing system 3 in accordance with the present embodiment, the processor 10 performs display so as to superimpose, on the endoscope image, the guide display indicating between the twelve o'clock direction and the eleven o'clock direction when the estimated summit line extends in the twelve o'clock direction centered on one end of the estimated summit line on the papillary orifice side (steps S364 and S400). The same applies to the case where the method in accordance with the present embodiment is implemented as the processing method. That is, in the processing method in accordance with the present embodiment, performed is display processing so as to superimpose, on the endoscope image, the guide display indicating between the twelve o'clock direction and the eleven o'clock direction when the estimated summit line extends in the twelve o'clock direction centered on one end of the estimated summit line on the papillary orifice side (steps S364 and S400). This configuration can facilitate a safer incision treatment when the incision treatment by the EST is performed. For example, since an incision operation by the EST is a manual operation, an error can occur and there is a possibility that the shift of the incision direction toward a one o'clock direction with respect to the above-mentioned twelve o'clock direction causes damage on an artery. To address this, the application of the method in accordance with the present embodiment allows the incision direction to be guided toward the eleven o'clock side, and can thereby decrease a possibility for causing damage on the artery even if the error occurs in the incision operation in EST.

Alternatively, the present embodiment may further include defining a length of the guide display GM. Specifically, for example, the processing section 100 is configured as a configuration example illustrated in FIG. 37, a processing example illustrated in a flowchart in FIG. 38 is added to the processing example in FIG. 27, whereby the above-mentioned method can be implemented. The configuration example of the processing section 100 in FIG. 37 is different from the configuration example of the processing section 100 in FIG. 26 in further including the incision length estimation section 170. The incision length estimation section 170 further includes a hooding fold estimation section 180. Although not illustrated, the processing section 100 in FIG. 37 may have a configuration in which the processing section 100 in FIG. 29 further includes the incision length estimation section 170 and the like. In this case, the processing example illustrated in the flowchart in FIG. 38 is only required to be added to the processing example in FIG. 30.

The processing example indicated in the flowchart in FIG. 38 is now described. The processor 10 functions as the hooding fold estimation section 180, and performs processing of estimating a hooding fold (step S380).

Step S380 is performed with use of the trained model 22 that has been machine-learned. That is, the trained model 22 read out in a case where the processor 10 functions as the hooding fold estimation section 180 has been machine-learned to, for example, perform output with the depth map generated by the depth estimation section 110 as the input data and a region corresponding to the hooding fold in the depth map as the correct label. Although not illustrated, for example, the incision length estimation section 170 may receive the endoscope image from the display control section 50, and the trained model 22 may be machine-learned so as to perform output, with the endoscope image as the input data and the region corresponding to the hooding fold in the endoscope image as the correct label.

The processor 10 then functions as the incision length estimation section 170, and performs processing of estimating a rough indication of an incision length from position information of the hooding fold (step S390). Thereafter, the processor 10 performs step S400 in FIG. 8. With this configuration, for example, the endoscope image as indicated by B31 in FIG. 39 can be obtained. In the endoscope image indicated by B31, as a result of step S380, the region estimated to be the hooding fold is segmented as indicated by B32. Additionally, as a result of step S390, the guide display GM is displayed with a length from the papillary orifice indicated by B33 to the region of the hooding fold indicated by B32.

In this manner, in the processing system 3 in accordance with the present embodiment, the processor 10 estimates the position information of the hooding fold (step S380), estimates information of the incision length based on the estimated position information of the hooding fold (step S390), and performs display so as to superimpose the guide display GM with the length based on the estimated incision length on the endoscope image. The same applies to the case where the method in accordance with the present embodiment is implemented as the processing method. That is, in the processing method in accordance with the present embodiment, the processing of estimating the position information of the hooding fold is further performed (step S380), the processing of estimating the information of the incision length based on the estimated position information of the hooding fold is further performed (step S390), and the display processing so as to superimpose the guide display GM with the length based on the estimated incision length on the endoscope image is performed (step S400). With this configuration, the user can perform the EST with reference to the estimated position information of the hooding fold. This allows the user to perform the EST so as to set an incision range of the EST within small incision or middle incision while avoiding large incision. As a result, excessive bleeding, perforation, or the like can be prevented. Note that the small incision has an incision range that does not exceed the hooding fold, the large incision has an incision range until the edge of the upper side of the oral protrusion, and the middle incision has a middle incision range between the small incision and the large incision.

As illustrated in FIG. 40, the incision length estimation section 170 may further include a hooding fold estimation execution possibility determination section 182 and an alarm information generation section 184. In this case, the processing example in FIG. 38 may be modified into a processing example described in a flowchart in FIG. 41.

The processing example described in the flowchart in FIG. 41 is now described. A description about processing that is similar to that in FIG. 38 is omitted as appropriate. The processor 10 performs the above-mentioned step S380, and thereafter functions as the hooding fold estimation execution possibility determination section 182 to perform processing of determining whether or not a probability of estimation to be the hooding fold is a predetermined value or higher (step S382).

In a case where the probability of estimation to be the hooding fold is less than the predetermined value (NO in step S382), the processor 10 then functions as the alarm information generation section 184 to generate alarm information (step S384). For example, the processor 10 displays the probability of estimation to be the hooding fold as indicated by B34 in FIG. 39 and may further perform processing of displaying that the probability of estimation is less than the predetermined value or may perform processing of issuing a predetermined alarm sound. A wide variety of a known method therefor can be applied. In a case where the probability of estimation to be the hooding fold is not more than the predetermined value, it is highly likely that a region that is different from the region indicated by B32 is the actual hooding hold. Hence, even if the EST is performed with the incision length indicated by the guide display GM to be displayed, there is a possibility that incision is performed with a range larger than a desired range. In this regard, the application of the method in accordance with the present embodiment can prevent incision with an unintended range. On the other hand, in a case where the probability of estimation to be the hooding fold is the predetermined value or more (YES in step S382), the processor 10 performs the above-mentioned step S390.

Alternatively, the incision length estimation section 170 may include an incision length reduction section 186 in substitution for the alarm information generation section 184 as illustrated in FIG. 42. In this case, the processing example in FIG. 38 may be modified into a processing example indicated in a flowchart in FIG. 43.

The processing example indicated in the flowchart in FIG. 43 is now described. Note that a description of processing similar to that in FIGS. 38 and 41 is omitted as appropriate. The processor 10 performs the above-mentioned treatment in steps S380 and S382. In a case where the probability of estimation to be the hooding fold is less than the predetermined value (NO in step S382), the processor 10 then functions as the incision length estimation section 170 including the incision length reduction section 186, and performs processing of estimating the rough indication of the incision length from the position information of the hooding fold and reducing the estimated rough indication of the incision length (step S386). The processor 10 then performs processing in step S400 in FIG. 8. As described above with reference to FIG. 41, in a case of NO in step S382, it is highly likely that a region that is larger than the estimated region of the hooding fold and that is indicated by B32 in FIG. 39 is the region of the actual hooding fold. Although not illustrated, the processor 10, for example, obtains a length from the papillary orifice to the hooding fold, and displays the guide display GM with a length that is reduced from the length by a certain rate. With this configuration, in a case where the accuracy in estimating the region of the hooding fold is not sufficient, it is possible to decrease a possibility that incision is performed with a range larger than the desired range.

While the methods performed by the processing sections 100 in FIGS. 26, 32, and 37 have been individually described, these methods can be combined as appropriate. For example, as illustrated in FIG. 44, the processing section 100 can have a configuration including, in addition to the depth estimation section 110 and the summit line estimation section 120, the papillary orifice detection section 150, the incision region generation section 160, and the incision length estimation section 170. Similarly, although not illustrated, the processing section 100 can also have a configuration including, in addition to the depth estimation section 110 and the summit line estimation section 120, the treatment tool detection section 152, the incision region generation section 160, and the incision length estimation section 170.

Although the embodiments to which the present disclosure is applied and the modifications thereof have been described above, the present disclosure is not limited to the embodiments and the modifications thereof, and various modifications and variations in components may be made in implementation without departing from the spirit and scope of the present disclosure. The plurality of components disclosed in the embodiments and the modifications described above may be combined as appropriate to implement the present disclosure in various ways. For example, some of all the components described in the embodiments and the modifications may be deleted. Furthermore, components in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The invention claimed is:

1. A processing system comprising:
   a processor including hardware,
   the processor being configured to:
      acquire an endoscope image in which a duodenal papilla including an oral protrusion is imaged;
      estimate a depth map of a region including the duodenal papilla from the endoscope image;
      estimate a summit line of the oral protrusion from the estimated depth map, wherein the summit line is a linear region corresponding to a ridge line of the oral protrusion; and
      superimpose a guide display based on the estimated summit line on the endoscope image.

2. The processing system as defined in claim 1, wherein the guide display is an incision guide display in endoscopic sphincterotomy (EST).

3. The processing system as defined in claim 1, further comprising a memory that stores a trained model that has been trained to estimate the depth map from an input image,
   wherein the processor inputs the endoscope image to the trained model to estimate the depth map.

4. The processing system as defined in claim 1, wherein the processor estimates the summit line based on a first endoscope image in a state where a treatment tool is not inserted and a second endoscope image in a state where the treatment tool is inserted.

5. The processing system as defined in claim 4, wherein the processor estimates the summit line based on a difference between a first depth map estimated from the first endoscope image and a second depth map estimated from the second endoscope image.

6. The processing system as defined in claim 4, further comprising a memory that stores a trained model that has been trained to estimate the depth map from an input image,
   wherein the processor:
      inputs the first endoscope image to the trained model to estimate a first depth map, inputs the second endoscope image to the trained model to estimate a second depth map, and estimates the summit line based on the first depth map and the second depth map.

7. The processing system as defined in claim 6, wherein the processor estimates the summit line based on a difference between the first depth map and the second depth map in a state where a position of the duodenal papilla seen in the first endoscope image and a position of the duodenal papilla seen in the second endoscope image are aligned with each other.

8. The processing system as defined in claim 1, wherein; the processor:

detects a papillary orifice based on the endoscope image, and estimates the summit line starting from the papillary orifice.

9. The processing system as defined in claim 1, wherein: the processor:

detects a portion of a treatment tool seen in the endoscope image based on the endoscope image, and estimates the summit line starting from a tip of the detected portion.

10. The processing system as defined in claim 1, wherein the processor superimpose, on the endoscope image, the guide display indicating between a twelve o'clock direction and an eleven o'clock direction when the estimated summit line extends in the twelve o'clock direction centered on one end of the estimated summit line on a papillary orifice side.

11. The processing system as defined in claim 1, wherein: the processor:

estimates position information of a hooding fold, estimates information about an incision length based on the estimated position information of the hooding fold, and superimpose the guide display having a length based on the estimated incision length on the endoscope image.

12. The processing system as defined in claim 1, wherein; the processor:

estimates whether or not an intraluminal pressure of a duodenum is within a range of an appropriate pressure based on the endoscope image, and in a case where the intraluminal pressure of the duodenum is outside the range of the appropriate pressure, performs insufflation processing or deaeration processing so that the intraluminal pressure of the duodenum is within the range of the appropriate pressure.

13. An endoscope system comprising:

the processing system as defined in claim 1; and an endoscope.

14. A processing method comprising:

acquiring an endoscope image in which a duodenal papilla including an oral protrusion is imaged;

estimating a depth map of a region including the duodenal papilla from the endoscope image;

estimating a summit line of the oral protrusion from the estimated depth map, wherein the summit line is a linear region corresponding to a ridge line of the oral protrusion; and superimposing a guide display based on the estimated summit line on the endoscope image.

15. The processing method as defined in claim 14, wherein the guide display is an incision guide display in EST.

16. The processing method as defined in claim 14, further comprising estimating the summit line based on a first endoscope image in a state where a treatment tool is not inserted and a second endoscope image in a state where the treatment tool is inserted.

17. The processing method as defined in claim 16, further comprising estimating the summit line based on a difference between a first depth map estimated from the first endoscope image and a second depth map estimated from the second endoscope image.

18. The processing method as defined in claim 17, further comprising estimating the summit line based on a difference between the first depth map and the second depth map in a state where a position of the duodenal papilla seen in the first endoscope image and a position of the duodenal papilla seen in the second endoscope image are aligned with each other.

19. The processing method as defined in claim 14, further comprising:

detecting a papillary orifice based on the endoscope image, and estimating the summit line starting from the papillary orifice.

20. The processing method as defined in claim 14, further comprising:

estimating position information of a hooding fold;

estimating information about an incision length based on the estimated position information of the hooding fold; and superimposing the guide display having a length based on the estimated incision length on the endoscope image.

\* \* \* \* \*